United States Patent [19]
Ham et al.

[11] Patent Number: 5,834,494
[45] Date of Patent: Nov. 10, 1998

[54] PYRIDYLCARBAMOYL INDOLINES

[75] Inventors: Peter Ham, Harlow; Graham Elgin Jones; Ian Thomson Forbes, both of Hertfordshire, all of England

[73] Assignee: SmithKline Beecham p.l.c., Brentford, United Kingdom

[21] Appl. No.: 717,957

[22] Filed: Sep. 23, 1996

Related U.S. Application Data

[63] Continuation of Ser. No. 454,811, filed as PCT/EP94/02148, Jun. 30, 1994, abandoned.

[30] Foreign Application Priority Data

Jul. 6, 1993 [GB] United Kingdom ............... 9313913

[51] Int. Cl.$^6$ .................... C07D 401/12; A61K 31/44
[52] U.S. Cl. ................. 514/339; 546/278.1; 546/159; 548/245; 514/314; 514/378
[58] Field of Search ............ 546/278.1; 514/339

[56] References Cited

U.S. PATENT DOCUMENTS 4,428,881  1/1984  Hedrich et al. .................. 548/491

FOREIGN PATENT DOCUMENTS

WO 92/05170  4/1992  WIPO .
WO 94/04533  3/1994  WIPO .

OTHER PUBLICATIONS

Atwal et al., CA 121:230675, 1994.

*Primary Examiner*—Jane Fan
*Attorney, Agent, or Firm*—Soma G. Simon; Charles M. Kinzig; Edward T. Lentz

[57] ABSTRACT

Compounds of formula (I), processes for their preparation and their use in medicine are disclosed:

(I)

wherein:

P represents phenyl, a quinoline or isoquinoline residue, or a 5-membered or 6-membered aromatic heterocyclic ring containing up to three heteroatoms selected from nitrogen, oxygen or sulphur;

$R^1$ is hydrogen, $C_{1-6}$ alkyl, halogen, $CF_3$, $NR^7R^8$ or $OR^9$ where $R^7$, $R^8$ and $R^9$ are independently hydrogen, $C_{1-6}$ alkyl or aryl$C_{1-6}$alkyl;

$R^2$ is hydrogen or $C_{1-6}$ alkyl;

$R^3$ is $C_{1-6}$ alkyl;

n is 0 to 3;

m is 0 to 4; and $R^4$ groups are independently $C_{1-6}$ alkyl optionally substituted by one or more halogen atoms, $C_{2-6}$ alkenyl, $C_{2-6}$ alkynyl, $C_{3-6}$ cycloalkyl, $C_{3-6}$ cycloalkyl-$C_{1-6}$ alkyl, $C_{1-6}$ alkylthio, $C_{3-6}$cycloalkylthio, $C_{3-6}$ cycloalkyl$C_1C_6$ alkylthio, halogen, nitro, $CF_3$, $OCF_3$, $SCF_3$, $SO_2CF_3$, $SO_2F$, formyl, $C_{2-6}$ alkanoyl, cyano, optionally substituted phenyl or thienyl, $NR^7R^8$, $CONR^7R^8$, or $OR^9$ where $R^7$, $R^8$ and $R^9$ are as defined for $R^1$, $CO_2R^{10}$ where $R^{10}$ is hydrogen or $C_{1-6}$ alkyl.

6 Claims, No Drawings

PYRIDYLCARBAMOYL INDOLINES

This is a continuation of application Ser. No. 08/454,811, filed as PCT/EP94/02148, Jun. 30, 1994, now abandoned.

This invention relates to compounds having pharmacological activity, processes for their preparation, to compositions containing them and to their use in the treatment of CNS disorders.

WO 94/04533 (SmithKline Beecham plc) describes indole and indoline derivatives which are described as possessing $5HT_{2C}$ receptor antagonist activity. A structurally distinct class of compounds has now been discovered, which have been found to have $5HT_{2C}$ receptor antagonist activity. Certain compounds of the invention also exhibit $5HT_{2B}$ antagonist activity. $5HT_{2C/2B}$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

The present invention therefore provides, in a first aspect, a compound of formula (I) or a salt thereof:

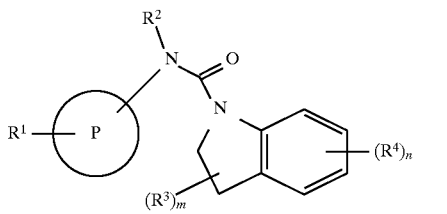

wherein:

P represents phenyl, a quinoline or isoquinoline residue, or a 5-membered or 6-membered aromatic heterocyclic ring containing up to three heteroatoms selected from nitrogen, oxygen or sulphur, $R^1$ is hydrogen, $C_{1-6}$ alkyl, halogen, $CF_3$, $NR^7R^8$ or $OR^9$ where $R^7$, $R^8$ and $R^9$ are independently hydrogen, $C_{1-6}$ allyl or aryl$C_{1-6}$alkyl;

$R^2$ is hydrogen or $C_{1-6}$ alkyl;

$R^3$ is $C_{1-6}$ alkyl;

n is 0 to 3;

m is 0 to 4; and $R^4$ groups are independently $C_{1-6}$ alkyl optionally substituted by one or more halogen atoms, $C_{2-6}$ alkenyl, $C_{2-6}$ alkynyl, $C_{3-6}$ cycloalkyl, $C_{3-6}$ cycloalkyl-$C_{1-6}$ allyl, $C_{1-6}$ alkylthio, $C_{3-6}$cycloalkylthio, $C_{3-6}$ cycloalkyl$C_{1-6}$ alkylthio, halogen, nitro, $CF_3$, $OCF_3$, $SCF_3$, $SO_2CF_3$, $SO_2F$, formyl, $C_{2-6}$ alkanoyl, cyano, optionally substituted phenyl or thienyl, $NR^7R^8$, $CONR^7R^8$, or $OR^9$ where $R^7$, $R^8$ and $R^9$ are as defined for $R^1$, $CO_2R^{10}$ where $R^{10}$ is hydrogen or $C_{1-6}$ alkyl.

$C_{1-6}$ Alkyl groups, whether alone or as part of another group, may be straight chain or branched.

The urea moiety can be attached to a carbon or any available nitrogen atom of the ring P, preferably it is attached to a carbon atom. Suitable moieties when the ring P is a 5-membered aromatic heterocyclic ring include isothiazolyl, isoxazolyl, thiadiazolyl and triazolyl. Suitable moieties when the ring P is a 6-membered aromatic heterocyclic ring include, for example, pyridyl, pyrimidyl or pyrazinyl. When P is quinoline, or an isoquinoline residue, the urea moiety can be attached at any position of the ring, preferably to the 4- or 5-position. Preferably P is 3-pyridyl.

Preferably $R^1$ is hydrogen.

Preferably $R^2$ and $R^3$ are hydrogen.

When $R^4$ is phenyl or thienyl, optional substituents include those listed above for $R^1$. Preferred $R^4$ groups include $C_{1-6}$ alkyl, $C_{1-6}$ alkylthio, halogen, $CF_3$, and $CO_2R^{10}$ where $R^{10}$ is hydrogen or $C_{1-6}$ alkyl. When n is greater than 1 the resulting $R^4$ groups can be the same or different. Preferably n is 2, the indoline ring being disubstituted in the 5- and 6-positions. Most preferably the 6-position is substituted by chloro, bromo, or iodo, and the 5-position is substituted by $C_{1-6}$alkyl, in particular methyl, ethyl, propyl and isopropyl, or $C_{1-6}$alkylthio, in particular thiomethyl and thioethyl.

It will be appreciated by those skilled in the art that when m is greater than 1 the resulting allyl groups can be the same or different and can, if desired, be attached to the same carbon atom.

Particular compounds of the invention include:
5-Ethylthio-1-(3-pyridylcarbamoyl)indoline,
6-Chloro-5-methyl-1-(3-pyridycarbamoyl)indoline,
6-Chloro-5-methyl-1-(3-pyridylcarbamoyl)indoline and 4chloro-5-methyl-1-(3-pyridylcarbamoyl)indoline,
5-(N,N-Dimethylamino)-1-(3-pyridylcarbamoyl)indoline,
5-Iodo-1-(3-pyridylcarbamoyl)indoline,
5-Nitro-1-(3-pyridylcarbamoyl)indoline,
5-Methylthio-1-(3-pyridylcarbamoyl)indoline,
5-(2-Isoropyl)-1-(3-pyridylcarbamoyl)indoline,
4,6-Dichloro-5-methyl-1-(3-pyridylcarbamoyl)indoline,
6-Fluoro-5-methyl-1-(3-pyridylcarbamoyl)indoline,
6-Iodo-5-methyl-1-(3-pyridylcarbamoyl)indoline,
4-Iodo-5-methyl-1-(3-pyridylcarbamoyl)indoline,
6-Bromo-5-methyl-1-(3-pyridylcarbamoyl)indoline,
4-Bromo-5-methyl-1-(3-pyridylcarbamoyl)indoline,
5-Phenyl-1-(3-pyridylcarbamoyl)indoline,
4,5-Dichloro-1-(3-pyridylcarbamoyl)indoline,
6,7-Dichloro-1-(3-pyridylcarbamoyl)indoline,
5-Chloro-1-(3-pyridylcarbamoyl)indoline,
6-Chloro-1-(3-pyridylcarbamoyl)indoline,
5,6-Dichloro-1-(3-pyridylcarbamoyl)indoline,
5-(3-Thienyl)-1-(3-pyridylcarbamoyl)indoline,
5-Trifluoromethyl-1-(3-pyridylcarbamoyl)indoline,
5-Chloro-6-methyl-1-(3-pyridylcarbamoyl)indoline,
6-Chloro-5-methyl-1-(2-methyl-4-quinolyl-1-carbamoyl) indoline,
6-Chloro-5-methyl-1-(4-pyridyl-carbamoyl)indoline,
6-Chloro-5-methyl-1-(5-quinolylcarbamoyl)indoline,
6-Chloro-5-methyl-1-(3-methyl-5-isoxazolylcarbamoyl) indoline,
5-(N,N-Dimethylamino)-1-(2-methyl-4-quinolinylcarbamoyl)indoline,
6-Chloro-5-methylthio-1-(3-pyridylcarbamoyl)indoline,
4-Chloro-5-methylthio-1-(3-pyridylcarbamoyl)indoline,
5-Bromo-1-(3-pyridylcarbamoyl)indoline,
6-Chloro-5-ethyl-1-(3-pyridylcarbamoyl)indoline,
6-Chloro-5-propyl-1-(3-pyridylcarbamoyl)indoline,
6-Chloro-5-tert-butyl-1-(3-pyridylcarbamoyl)indoline,
4-Chloro-5-tert-butyl-1-(3-pyridylcarbamoyl)indoline,
6-Chloro-5-isopropyl-1-(3-pyridylcarbamoyl)indoline,
6-Chloro-5-vinyl-1-(3-pyridylcarbamoyl)indoline,
6-Chloro-5-ethylthio-1-(3-pyridylcarbamoyl)indoline,
6-Chloro-5-isopropylthio-1-(3-pyridylcarbamoyl)indoline,
Methyl-6-chloro-1-(3-pyridylcarbamoyl)-indoline-5-carboxylate,
6-Chloro-5-iodo-1-(3-pyridylcarbamoyl)-indoline,
6-Chloro-5-methyl-1-(5-bromo-3-pyridylcarbamoyl)-indoline, 6-Bromo-5-propylthio-1-(3-pyridylcarbamoyl)indoline,
6-Bromo-5-ethylthio-1-(3-pyridylcarbamoyl)indoline,
6-Bromo-5-methylthio-1-(3-pyridylcarbamoyl)indoline,
and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form N-oxides or solvates such as hydrates, and the invention also extends to these forms. When referred to herein, it is understood that the term 'compound of formula (I)' also includes these forms.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (1) or a pharmaceutically acceptable salt thereof, which process comprises:
the coupling of a compound of formula (II);

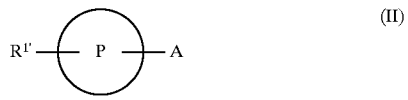

with a compound of formula (III);

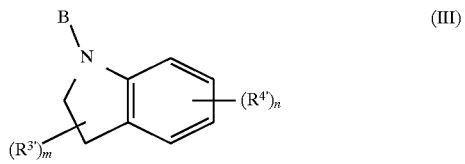

wherein n, m and P are as defined in formula (I), A and B contain the appropriate functional group(s) necessary to form the moiety —NR$^{2'}$CO when coupled, the variables R$^{1'}$, R$^{2'}$, R$^{3'}$ and R$^{4'}$ are R$^1$, R$^2$, R$^3$, and R$^4$ respectively, as defined in formula (1), or groups convertible thereto, and thereafter optionally and as necessary and in any appropriate order, converting any R$^{1'}$, R$^{2'}$, R$^{3'}$ and R$^{4'}$, when other than R$^1$, R$^2$, R$^3$, and R$^4$ respectively to R$^1$, R$^2$, R$^3$, and R$^4$, interconverting R$^1$, R$^2$, R$^3$, and R$^4$ and forming a pharmaceutically acceptable salt thereof.

Suitable examples of groups A and B include:
(i) A is —N=C=O and B is hydrogen,
(ii) A is —NR$^{2'}$COL and B is hydrogen,
(iii) A is —NHR$^{2'}$ and B is COL, or
(iv) A is halogen and B is —CONHR$^{2'}$
wherein R$^{2'}$ is as defined above and L is a leaving group. Examples of suitable leaving groups L include halogen such as chloro, bromo, imidazole, phenoxy or phenylthio optionally substituted, for example, with halogen.

When A is —N=C=O and B is hydrogen the reaction is suitably carried out in an inert solvent for example dichloromethane or toluene at ambient or elevated temperature.

When A is —NR2'COL and B is hydrogen or when A is —NHR2' and B is —COL, the reaction is suitably carried out in an inert solvent such as dichloromethane at ambient temperature optionally in the presence of a base, such as triethylamine or in dimethylformamide at ambient or elevated temperature.

When A is halogen and B is CONHR$^{2'}$, the reaction is suitably carried out in an inert solvent such as toluene at elevated temperature, optionally in the presence of a base.

It should be appreciated that P in formula (II) represents rings P as defined in relation to formula (I) in which R$^1$ is as defined in relation to formula (I) or groups convertible thereto i.e. R$^{1'}$.

R$^4$ groups can be introduced at any suitable stage in the process, preferably R$^4$ groups are introduced at an early stage in the process. It should be appreciated that it is preferred that all groups R$^1$ to R$^4$ are introduced before coupling compounds of formula (II) and (III).

Suitable examples of groups R$^{1'}$, R$^{2'}$, R$^{3'}$ and R$^{4'}$ which are convertible to R$^1$, R$^2$, R$^3$ and R$^4$ alkyl groups respectively, include acyl groups which are introduced conventionally and may be converted to the corresponding alkyl group by conventional reduction, such as using sodium borohydride in an inert solvent followed by hydrogenolysis in an inert solvent. Hydrogen substituents may be obtained from alkoxycarbonyl groups which may be converted to hydrogen by hydrolysis and decarboxylation. When R$^4$ is hydroxy it is preferably protected in the compound of formula (II) as, for example, benzyl which is removed by hydrogenation.

Suitable examples of a group R$^{2'}$ which are convertible to R$^2$, include alkoxycarbonyl and benzyl or para-methoxybenzyl which are converted to the group where R$^2$ is hydrogen using conventional conditions.

Interconversions of R$^1$, R$^2$, R$^3$ and R$^4$ are carried out by conventional procedures. For example R$^1$ halo and R$^4$ halo may be introduced by selective halogenation of the ring P or the benzene ring of the indoline group using conventional conditions. It should be appreciated that it may be necessary to protect any R$^1$ to R$^4$ hydrogen variables which are not required to be interconverted.

Suitable protecting groups and methods for their attachment and removal are conventional in the art of organic chemistry, such as those described in Greene T. W. 'Protective groups in organic synthesis' New York, Wiley (1981).

Compounds of formula (II) in which A is NHR$^{2'}$ are known compounds or can be prepared analogously to known compounds, see, for example, WO 92/05170 (SmithKline Beecham plc).

Compounds of formula (II) in which A is —N=C=O may be prepared by treating a compound of formula (II) in which:
i) A is amino, with phosgene or a phosgene equivalent, in the presence of excess base in an inert solvent.
ii) A is acylazide (i.e. CON$_3$), via the nitrene, by thermal rearrangement using conventional conditions (ref L. S. Trifonov et al, Helv. Chim. Acta 1987 70 262).
iii) A is CONH$_2$, via the nitrene intermediate using conventional conditions.

Compounds of formula (II) in which A is NR$^{2'}$COL may be prepared by reacting a compound of formula (II) in which A is NHR$^{2'}$ with phosgene or a phosgene equivalent in an inert solvent, at low temperature, if necessary in the presence of one equivalent of a base such as trithylamine.

Compounds of formula (III) may be prepared according to known methods or analogous to known methods, for example
a) from the appropriate aniline via indole formation (Nordlander [JOC, 1981, 778] or Sundberg [JOC 1984, 249] routes) followed by reduction of the indole ring using sodium cyanoborohydride. It will be appreciated that in certain cases a mixture of indoles will be formed which can be separated at this stage or at a later stage.
b) from the appropriate ortho-methyl nitrobenzene via indole formation (Leimgruber procedure Org Syn Coll vol VII, p34) followed by reduction of the indole ring.

c) by aromatic substitution of a suitably protected indole/indoline precursor, for example alkylthio groups maybe introduced by thiocyanation of the indoline ring followed by hydrolysis and alkylation, or d) by transition metal catalysed coupling reaction using a suitably substituted indole/indoline precursor for example vinylation using the Stille procedure (*JACS* 1987, 5478)

Compounds of formula (II) in which A is halogen and $R^{1'}$ is hydrogen are commercially available.

Novel intermediates of formula (III) also form part of the invention.

Pharmaceutically acceptable salts may be prepared conventionally by reaction with the appropriate acid or acid derivative. N-oxides may be formed conventionally by reaction with hydrogen peroxide or percarboxylic acids.

Compounds of formula (I) and their pharmaceutically acceptable salts have $5HT_{2B/2C}$ receptor antagonist activity and are believed to be of potential use fo the treatment or prophylasis of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

Description 1

Di-(5-indolinyl)disulphide (D1)

A mixture of indoline (5.95 g, 50 mmol) and potassium thiocyanate (9.7 g, 100 mmol) in dry methanol (100 ml) was cooled to 0° C., and a solution of bromine (2.0 ml, 52.5 mmol) in methanol (100 ml) was added over 15 mins. The mixture was then stirred at 0° C. for 1 h 15 mins, and then warmed to room temperature over 30 mins. The mixture was filtered, diluted with water (200 ml) and 10% sodium hydroxide (20 ml) was added. The mixture was stirred overnight at room temperature, then extracted with dichloromethane. The aqueous phase was neutralised by addition of 5M hydrochloric acid and extracted again with dichloromethane. Organic extracts were separately evaporated and residues separately chromatographed on silica (200 g) eluted with dichloromethane/methanol to give the title compound (3.32 g total, 44%) as a gum.

NMR (CDCl$_3$) δ: 3.00 (2H, t, J=9), 3.58 (2H, t, J=9), 6.50 (1H, d, J=8), 7.10 (1H, d, J=8), 7.23 (1H, s).

Description 2

1,1'-Diacetyldi-(5-indolinyl)disulphide (D2)

To a solution of disulphide (D1, 3.87 g, 12.9 mmol) in dry dichloromethane (60 ml) was added triethylamine (4.2 ml, 30 mmol) and acetic anhydride (2.7 ml, 28.4 mmol). The mixture was stirred overnight at room temperature, then washed twice with water, dried and evaporated. The residue was recrystallised from dichloromethane/petrol to give the title compound (3.81 g, 77%), mp 187°–193° C.

NMR (CDCl$_3$) δ: 2.24 (3H, s), 3.19 (2H, t, J=9), 4.08 (2H, t, J=9), 7.27 (1H, s), 7.30 (1H, d, J=8) 8.03 (1H, d, J=8).

Description 3

1-Acetyl-5-mercaptoindoline (D3)

A mixture of disulphide (D2, 3.8 g, 9.9 mmol), triphenylphosphine (2.9 g, 11 mmol) and conc. hydrochloric acid (3 drops) in 1,4-dioxan (30 ml) and water (6 ml) was stirred at 50°–60° C. for 4.5 h. The mixture was evaporated and the residue was dissolved in dichloromethane and extracted with dilute sodium hydroxide solution. The basic extract was carefully acidified with conc. hydrochloric acid, and extracted with dichloromethane. This extract was dried and evaporated to give the title compound (3.38 g, 88%) as a gum.

NMR (CDCl$_3$) δ: 2.24 (3H, s), 3.15 (2H, t, J=9), 3.43 (1H, s), 4.05 (2H, t, J=9), 7.13 (1H, s), 7.14 (1H, d, J=8), 8.09 (1H, d, J=8).

Description 4

2-Trifluoromethylsulphonyloxyacetaldehyde Diethyl Acetal (D4)

A solution of glycolaldehyde diethyl acetal (6 g, 44.8 mmol) and triethylamine (7.05 ml, 50 mmol) in dry dichloromethane (50 ml) was cooled to −78° C. A solution of trifuoromethanesulphonic anhydride (13.9 g, 49.2 mmol) in dichloromethane (50 ml) was added dropwise over 30 mins. The mixture was stirred at −78° C. for 1 h, then washed twice with water, dried and evaporated to give the title compound (10.64 g, 89%) as an oil.

NMR (CDCl$_3$) δ: 1.25 (6H, t, J=7), 3.61 (2H, m), 3.77 (2H, m), 4.40 (2H, d, J=6), 4.75 (1H, t, J=6)

Description 5

1-Acetyl-5-(2,2-diethoxyethylthio)indoline (D5)

A mixture of thiol (D3, 3.38 g, 17.5 mmol), acetal trifluoromethanesulphonate (D4, 5.05 g, 19 mmol) and diisopropylethylamine (3.2 ml, 19 mmol) in dry dichloromethane (80 ml) was stirred for 4.5 h at room temperature. Further small portions of trifluoromethane sulphonate and of DIPEA (2 drops each) were added and stirring was continued for another 1 h before the mixture was washed sequentially with dilute hydrochloric acid, dilute sodium hydroxide, and water. The organic phase was dried and evaporated, and the residue was chromatographed on silica (300 g) eluted with ethyl acetate to give the title compound (4.14 g, 76.6%), as a waxy solid, mp <52° C.

NMR (CDCl$_3$) δ: 1.20 (6H, t, J=7), 2.21 (3H, s), 3.07 (2H, d, J=6), 3.18 (2H, t, J=8), 3.56 (2H, q, J=7), 3.65 (2H, q, J=7), 4.06 (2H, t, J=8), 4.51 (1H, t, J=6), 7.26 (2H, m), 8.12 (1H, d, J=8)

Description 6

N-Acetyl-5-ethylthioindoline (D6)

To a solution of acetal (D5, 2.14 g, 6.9 mmol) in dry dichloromethane (80 ml) at −78° C. was added titanium tetrachloride (1.48 ml, 13.85 mmol) dropwise by syringe. The mixture was stirred for 2 h at −78° C., 2 h at 0° C. and then overnight at room temperature. The mixture was then washed with water, saturated sodium bicarbonate solution, then water again, dried and evaporated. The residue was taken up in hot dichloromethane and petrol was added to precipitate polar material as a gum. The liquor was decanted off and addition of petrol/decantation was repeated twice. The final liquor was evaporated to give a mixture of the title compound and 5-acetyl-6,7-dihydro-5H-thieno[2,3-f]indole (0.31 g), which was hydrolysed without separation.

Description 7

5-Ethylthioindoline (D7)

The product mixture from description 6 was heated under reflux overnight with 10% aqueous sodium hydroxide (25 ml) and ethanol (5 ml). After cooling, the mixture was diluted with water and extracted with dichloromethane. The organic extract was washed with water, dried and evaporated. The residue was chromatographed on silica gel (5 g) eluted with 3% methanol/dichloromethane to remove polar material, and then centrifugally chromatographed on a 1 mm silica plate eluted with 1:1 ether/petrol to give the title compound (70 mg), as a gum.

NMR (CDCl$_3$) δ: 1.25 (3H, t, J=7), 2.79 (2H, q, J=7), 3.03 (2H, t, J=8), 3.59 (2H, t, J=8), 6.58 (1H, d, J=8), 7.12 (1H, d, J=8), 7.22 (1H, s)

Description 8

N-(3-Chloro4-methylphenyl)-2,2-diethoxyethylamine (D8)

3-Chloro-4-methylaniline (10.26 g, 72.5 mmol), sodium hydrogen carbonate (9.1 g, 108 mmol) and bromoacetaldehyde diethyl acetal (13.1 ml, 87.1 mmol) were stirred at reflux under Ar in ethanol (150 ml) for 6 days. The mixture was then evaporated to dryness, partitioned between ether and water, and separated. The organic portion was washed with brine, dried (Na$_2$SO$_4$) and evaporated to a black oil. Bulb to bulb distillation of this crude material (oven temperature 175° C., ca 0.1 mmHg) then gave the title compound (4.90 g, 26%) as a colourless oil.

NMR (CDCl$_3$) δ: 1.23 (6H, t, J=7), 2.25 (3H, s), 3.22 (2H, d, J=6), 3.5–3.8 (4H, m), 4.70 (1H, t, J=6), 6.53 (1H, dd, J=8, 2), 6.72 (1H, d, J=2), 7.01 (1H, d, J=8)

Description 9

6-Chloro-5-methylindole and 4-chloro-5-methylindole (D9)

N-(3-chloro4-methylphenyl)-2,2-diethoxyethylamine (D8) (4.90 g, 19 mmol) was stirred in trifluoroacetic acid (25 ml), and trifluoroacetic anhydride (25 ml) was added. The solution was stirred for 30 min, diluted with trifluoroacetic acid (35 ml), and stirred at reflux under Ar for 64 h. Evaporation to dryness then gave a dark syrup, which was dissolved in methanol (50 ml). Anhydrous potassium carbonate (5.25 g, 38 mmol) was added, and the mixture was stirred for 1 h, diluted with (250 ml), and stirred until the emulsion had coagulated (30 min). The semi-solid was filtered off and air-dried. Chromatography on silica, eluting with chloroform, gave the title mixture of compounds (0.88 g, 28%), in approximate proportions 3:2, as a brown solid. Further chromatography on silica gel, eluting with 0–4% ethyl acetate in petroleum ether (b.p. 60°–80° C.) gave pure 6-chloro isomer (0.11 g), and the remainder (0.69 g) still as a mixture.

6-chloro isomer: NMR (CDCl₃) δ: 2.45 (3H, s), 6.46 (1H, m), 7.14 (1H, m), 7.38 (1H, s), 7.47 (1H, s), 8.02 (1H, b)

4-chloroisomer (as component of mixture): NMR (CDCl₃) δ: 2.47 (3H, s), 6.62 (1H, m), 7.0–7.2 (3H, m), 8.1 (1H, b)

Description 9 (Alternative Procedure)

6-Chloro-5-methyl Indole

An equal mixture of 6-chloro-5-methyl indole and 4-chloro-5-methyl indole was prepared from 3-chloro-4-methyl-aniline using the method of Sundberg. Crystallisation of this mixture (6.8 g) afforded pure 6-chloro-5-methyl indole as a white crystalline solid (2.5 g).

NMR (CDCl₃) δ: 2.45 (3H, s), 6.45 (1H, bs), 7.20 (1H, t, J 3Hz), 7.40 (1H, s), 7.50 (1H, s), 8.1 (1H, bs).

Description 10

6-Chloro-5-methylindoline (D10)

6-Chloro-5-methylindole (D9) (0.109 g, 0.66 mmol) was stirred at 15° C. in glacial acetic acid (3 ml), and sodium cyanoborohydride (0.125 g, 1.98 mmol) was added. The mixture was stirred at 15° C. for 2 h, diluted with water (40 ml), basified with solid NaOH, and extracted with ether. The extract was dried (Na₂SO₄) and evaporated to give the title compound (0.105 g, 95%) as a light yellow solid.

NMR (CDCl₃) δ: 2.44 (3H, s), 2.95 (2H, t, J=8), 3.54 (2H, t, J=8), 6.62 (1H, s), 6.94 (1H, s)

Description 11

6-chloro-5-methylindoline and 4-chloro-5-methylindoline (D11)

These were prepared, as a mixture, from the mixture of 6-chloro-5-methylindole and 4-chloro-5-methylindole (0.40 g, 2.4 mmol), prepared as described in Description 9, following the procedure of Description 10. This gave a mixture of the title compound (0.37 g, 91%) in approximate proportions 3:2.

4-chloroisomer (as component of mixture): NMR (CDCl₃) δ 2.27 (3H, s), 3.07 (2H, t, J=8), 3.59 (2H, t, J=8), 6.44 (1H, d, J=8), 6.88 (1H, d, J=8).

Description 12

1-Acetyl-5-(N,N-dimethylamino)indoline (D12)

1-Acetyl-5-nitroindoline (0.9 g, 4.37 mol), EtOH (15 ml), 37% aqueous formaldehyde (1 ml), and 10% Pd-C (0.1 g) were mixed and hydrogenated at 45 psi and rt overnight. The mixture was filtered through celite and evaporated to dryness under reduced pressure to afford the title compound (0.89 g, 100%).

NMR (CDCl₃) δ: 2.20 (3H, s), 2.92 (6H, s), 3.18 (3H, t), 4.02 (2H, t), 6.61 (2H, m), 8.08 (1H, d).

Description 13

5-(N,N-Dimethylamino)indoline

1-Acetyl-5-(N,N-dimethylamino)indoline (D12) (0.6 g, 2.94 mmol) in conc. HCl (0.6 ml) was heated over a steam bath for 45 min. The mixture was partitioned between sat aq. K₂CO₃ (50 ml) and CHCl₃ (50 ml) the organic solution dried (Na₂SO₄), evaporated to dryness under reduced pressure and purified by column chromatography (SiO₂, EtOAc/MeOH 5–10%) to afford the title compound (290 mg, 61%) which was used directly in Example 4.

Description 14

1-Acetyl-5-methylthioindoline (D14)

A mixture of 1-acetyl-5-mercaptoindoline (D3) (0.98 g, 5.07 mmol), methyl iodide (0.35 ml, 5.6 mmol) and triethylamine (0.78 ml, 5.6 mmol) in dichloromethane (25 ml) was stirred for 18 h at room temperature. The mixture was evaporated, and the residue was redissolved in dichloromethane and washed with dilute hydrochloric acid. The organic solution was dried and evaporated to give the title compound (0.98 g, 93%).

NMR (CDCl₃) δ: 2.22 (3H, s), 2.48 (3H, s), 3.18 (2H, t, J=8), 4.07 (2H, t, J=8), 7.12 (2H, m), 8.14 (1H, d, J=9)

Description 15

N-(2,2-Dimethoxyethylamino)-4-(2-propyl)aniline (D15)

A mixture of 4-(2-propyl)aniline (20.4 g, 151 mmol) and 2,2-dimethoxyethanal (49.8 g, 196 mmol) in ethanol (400 ml) was stirred with 5% palladium on charcoal (5 g) under hydrogen (1 atmos.) for 18 h. The mixture was then filtered through kieselguhr and evaporated. The residue was dissolved in ethyl acetate and washed with brine. The organic solution was dried and evaporated to give the title compound (33.69 g, 100%) as a red oil.

NMR (CDCl₃) δ: 1.20 (6H, d, J=6), 2.81 (1H, m, J=6), 3.22 (2H, d, J=5), 3.40 (6H, s), 3.75 (1H, broad), 4.58 (1H, t, J=5), 6.59 (2H, d, J=8), 7.05 (2H, d, J=8).

Description 16

5-(2-Propyl)-1-trifluoroacetyl Indole (D16)

The acetal (D15, 1.02 g, 4.55 mmol) was heated in trifluoroacetic acid/trifluoroacetic anhydride by the method of J. E. Nordlander et al (*J. Org. Chem*, 1981, 46, 778). The crude product was chromatographed twice on silica gel eluted with 1:1 dichloromethane/petrol to give the title compound (0.25 g, 22%).

NMR (CDCl₃) δ: 1.29 (6, d, J=7), 3.00 (1H, m, J=7), 6.68 (1H, d, J=5), 7.27 (1H, d, J=7), 7.42 (2H, s), 8.32 (1H, d, J=7).

Description 17

5-(2-propyl)indole (D17)

The trifluoroacetyl indole (D16, 0.25 g, 0.99 mmol) was stirred with potassium carbonate (0.20 g, 1.5 mmol) in methanol (7.5 ml) at 550 C for 1.5 h. Solvent was evaporated and the residue was partitioned between water and dichloromethane. The organic extract was dried and evaporated to give the title compound (0.14 g, 86%). NMR (CDCl₃) δ: 1.30 (6H, d, J=7), 3.00 (1H, m, J=7), 6.48 (1H, m), 7.01 (1H, m), 7.09 (1H, d, J=8), 7.20 (1H, d, J=8), 7.49 (1H, s), 7.71 (1H, broad).

Description 18

5-(2-Propyl)indoline (D18)

To a cooled solution of indole (D17, 0.60 g, 3.75 mmol) in glacial acetic acid (12 ml) was added sodium cyanoborohydride (1.20 g, 19.1 mmol) in portions. The mixture was stirred under argon for 4 h, then diluted with water and basified with 10% aqueous sodium hydroxide. The mixture was extracted with dichloromethane and the extract was dried and evaporated. After combining with material from a previous experiment (from 0.14 g indole) the crude product was chromatographed on silica gel eluted with diethyl ether to give the title compound (0.62 g, 84%).

NMR (CDCl$_3$) δ: 1.23 (6H, d, J=7), 2.81 (1H, m, J=7), 2.91 (2H, t, J=8), 3.38 (2H, t, J=8), 3.59 (1H, s), 6.47 (1H, d, J=8), 6.85 (1H, d, J=8), 6.98 (1H, s).

Description 19

5-Methylthioindoline (D19)

The N-acetylindoline (D14, 0.98 g, 4.73 mmol) was heated under reflux with 10% aqueous sodium hydroxide (75 ml) in ethanol (25 ml) for 21 h. After cooling, the mixture was extracted three times with dichloromethane, and the extracts were combined, dried and evaporated to give the title compound (0.66 g, 85%).

NMR (CDCl$_3$) δ: 1.62 (1H, broad), 2.42 (3H, s), 3.01 (2H, t, J=8), 3.58 (2H, t, J=8), 6.58 (1H, d, J=8), 7.07 (1H, d, J=8), 7.17 (1H, S).

Description 20

2,6-Dichloro-4-nitrotoluene (D20)

The title compound was prepared according to the route of Weinstock et al, patent U.S. Pat. No. 3,423,475.

NMR (250 MHz, CDCl$_3$) δ: 8.15 (s, 2H, Ar), 2.59 (s, 3H, CH$_3$).

Description 21

4-Amino-2,6-dichlorotoluene (D21)

To a stirred solution of SnCl$_2$ (3.7 g, 19.4 mmol) in conc. HCl (10 ml) was added portionwise (D20), (1 g, 4.8 mmol). The mixture was heated to 80° C. for 4 hours, cooled and made strongly basic with 40% NaOH. The aqueous was extracted into ether. The organics were dried and concentrated to afford the title compound as a light brown oil, 0.68 g (90%).

NMR (250 MHz, CDCl$_3$) δ: 6.60 (s, 2H, Ar), 3.63 (br, 2H, NH$_2$), 2.63 (s, 3H, —CH$_3$).

Description 22

4,6-Dichloro-5-methylindoline (D22)

The title compound was prepared from D21 according to Sundberg sequence of reactions, followed by reduction.

NMR (250 MHz, CDCl$_3$) δ: 6.52 (s, 1H, Ar), 3.80 (br, 1H, NH), 3.60 (t, 2H, J=8Hz), 3.10 (t, 2H, J=8Hz), 2.35 (s, 3H, CH$_3$)

Description 23

6-Fluoro-5-methylindole (D23)

The title compound was prepared from 3-fluoromethylaniline using the Sundberg sequence of reactions. (J.O.C. 1984, 49, 249)

Description 24

6-Fluoro-5-methylindoline (D24)

The title compound was prepared by reduction of 6-fluoro-5-methylindole (D23) using a procedure similar to that in Description 30.

NMR (CDCl$_3$) δ: 2.15 (3H, s), 2.95 (2H, t, J=8), 3.56 (2H, t, J=8), 6.31 (1H, d, J=8), 6.89 (1H, d, J=8).

Description 25

4-Iodo-5-methylindole and 6-iodo-5-methylindole (D25)

The title compounds were prepared as a mixture from 3-iodo-4-methylaniline using the Sundberg sequence of reactions. (J.O.C. 1984, 49, 249)

Description 26

4-Iodo-5-methylindoline and 6-iodo-5-methylindoline (D26)

The title compounds were prepared as a mixture by reduction of a mixture of 4-iodo-5-methylindole and 6iodo-5-methylindole (D25) using a procedure similar to Description 30.

Description 27

4-Bromo-5-methylindole and 6-bromo-5-methylindole (D27)

The title compounds were prepared as a mixture from 3-bromo-4methylaniline using the Sundberg sequence of reactions. (J.O.C. 1984, 42, 249)

Description 28

4-Bromo-5-methylindoline and 6-bromo-5-methylindoline (D28)

The title compounds were prepared as a mixture by reduction of a mixture of 4-bromo-5-methylindole and 6-bromo-5-methylindole (D27) using a procedure similar to Description 30.

Description 29

5-Phenyl Indole (D29)

The title compound was prepared from 5-bromoindole and benzeneboronic acid by the method of Suzuki (N. Miyaura, T Yanagi, A Suzuki, Synth. Commun, 1981, 513) in 87% yield.

NMR (CDCl$_3$) δ: 6.59–6.65 (1H, m), 7.21–7.50 (6H, m), 7.61–7.70 (2H, m), 7.86 (1H, s), 8.10–8.30 (1H, br s).

Description 30

5-Phenyl Indoline (D30)

5-Phenylindole (D29) (0.85 g, 4.4 mmoles) was dissolved in glacial acetic acid (20 ml) and treated with sodium cyanoborohydride (1.34 g, 22 mmoles) at ambient temperature for 2 hrs. Water (100 ml) was added and the mixture basified with sodium hydroxide. Extraction with dichloromethane gave the title compound (D30) (0.8 g, 93%).

NMR (CDCl$_3$) δ: 2.40–2.90 (1H, br s), 3.10 (2H, t, J=8), 3.65 (2H, t, J=8), 6.70 (1H, d, J=10), 7.20–7.65 (7H, m).

Description 31

4,5-Dichloroindole (D31)

4,5-dichlorisatin (8.4 g, 39 mmoles) was treated with lithium aluminium hydride (15.0 g, 390 mmoles) in tetrahydrofuran (500 ml) under reflux. Aqueous work up and treatment of the intermediate hydroxy indoline compound with p-toluene sulphonic acid in toluene gave the title compound (D31) (1.34 g, 19%).

NMR (CDCl$_3$) δ: 6.60–6.70 (1H, m), 7.19–7.35 (3H, m), 8.10–8.45 (1H, br s).

Description 32

4,5-Dichloroindoline (D32)

4,5-Dichloroindole (D31) was reduced in the usual way with sodium cyanoborohydride in glacial acetic acid to give the title compound (D32) (1.22 g, 90%)

NMR (CDCl$_3$) δ: 3.10 (2H, t, J=8), 3.61 (2H1, t, J=8), 3.76–3.91 (1H, br s), 6.41 (1H, d, J=10), 7.10 (1H, d, J=10).

Description 33

6,7-Dichloroindole (D33)

Reduction of 6,7-dichloroisatin with lithium aluminium hydride in the usual way gave the title compound (D33) (4.8 g, 62%).

NMR (CDCl$_3$) δ: 6.55–6.62 (1H, m), 7.20 (1H, d, J=8), 7.21–7.28 (1H, m), 7.49 (1H, d, J=8), 8.25–8.55 (1H, br s)

Description 34

6,7-Dichloroindoline (D34)

6,7-Dichloroindole (D33) was reduced in the usual way with sodium cyanoborohydride in glacial acetic acid to give the title compound (D34) (1.14 g, 67%).

NMR (CDCl$_3$) δ: 3.10 (2H, t, J=8), 3.65 (2H, t, J=8), 4.01–4.15 (1H, br s), 6.71 (1H, d, J=8), 6.81 (1H, d, J=8).

Description 35

5-Chloroindoline (D35)

5-Chloroindole was reduced in the usual way with sodium cyanoborohydride in glacial acetic acid to give the title compound (D35) (0.96 g, 94%)

NMR (CDCl$_3$) δ: 3.01 (2H, t, J=8), 3.55 (2H, t, J=8), 3.67–3.80 (1H, br s), 6.52 (1H, d, J=8), 6.93 (1H, d, J=8), 7.05 (1H, s).

Description 36

6-Chloroindoline (D36)

6-Chloroindole was reduced in the usual way with sodium cyanoborohydride in glacial acetic acid to give the title compound (D36) (1.18 g, 94%).

NMR (CDCl$_3$) δ: 2.95 (2H, t, J=8), 3.11 (2H, t, J=8), 3.70–3.93 (1H, br s), 6.60 (1H, s), 6.64 (1H, d, J=8), 6.99 (1H, d, J=8).

Description 37

2-Nitro-4,5-dichlorotoluene (D37)

Nitration of 3,4-dichlorotoluene in a mixture of concentrated sulphuric and nitric acids gave the title compound (D37) (4.2 g, 41%).

NMR (CDCl$_3$) δ: 2.60 (3H, s), 7.49 (1H, s), 8.15 (1H, s).

Description 38

5,6-Dichloroindole (D38)

The title compound was prepared using the Leimgruber procedure (A. D. Batcho, W. Leimgruber, Organic Synthesis Collective Volume (VIII), p34) on 2-nitro-4,5-dichlorotoluene (D37) to give (D38) (1.3 g, 72%).

NMR (CDCl$_3$) δ: 6.48–6.52 (1H, m), 7.22–7.25 (1H, m), 7.50 (1H, s), 7.73 (1H, s), 8.01–8.31 (1H, br s).

Description 39

5,6-Dichloroindoline (D39)

5,6-Dichloroindole (D38) was reduced in the usual way with sodium cyanoborohydride in glacial acetic acid to give the title compound (D39) (1.18 g, 90%).

NMR (CDCl$_3$) δ: 3.01 (2H, t, J=8), 3.63 (1H, t, J=8), 3.75–3.91 (1H, br s), 6.70 (1H, s), 7.15 (1H, s).

Description 40

5-(3-Thienyl) indole (D40)

The title compound was prepared as in (D29) from 5-bromoindole and thiophene-3-boronic acid to give (D40) (1.1 g, 100%).

NMR (CDCl$_3$) δ: 6.55–6.61 (1H, m), 7.19–7.51 (6H, m), 7.88 (1H, s), 8.10–8.28 (1H, br s).

Description 41

5-(3-Thienyl)indoline (D41)

5-(3-Thienyl)indole D40 was reduced in the usual way with sodium cyano borohydride in glacial acetic acid to give the title compound (D41) (1.0 g, 100%).

NMR (CDCl$_3$) δ: 3.09 (2H, t, J=8), 3.62 (2H, t, J=8), 3.70–3.92 (1H, br s), 6.68 (1H, d, J=6), 7.25–7.45 (5H, m).

Description 42

5-Trifluoromethylindole (D42)

The title compound was prepared from 4-aminobenzotrifluoride using the method of Sundberg to give (D42) (0.22 g).

NMR (CDCl$_3$) δ: 6.51–6.60 (1H, m), 7.21–7.30 (1H, m), 7.35–7.42 (2H, m), 7.88 (1H, S), 8.15–8.45 (1H, br s).

Description 43

5-Trifluoromethylindoline (D43)

5-Trifluoromethylindole (D42) was reduced in the usual way with sodium cyanoborohydride in glacial acetic acid to give the title compound (D43) (0.18 g, 83%)

NMR (CDCl$_3$ δ: 3.08 (2H, t, J=8), 3.65 (2H, t, J=8), 3.88–4.12 (1H, br s), 6.60 (1H, d, J=6), 7.23–7.35 (2H, m).

Description 44

5-Chloro-6-methylindole (D44)

The title compound was prepared using the Leimgruber procedure on 2-chloro-5-nitro para-xylene to give (D44) (0.64 g, 72%).

NMR (CDCl$_3$) δ: 2.65 (3H, s), 6.62–6.68 (1H, m), 7.30–7.34 (1H, m), 7.40 (1H, s), 7.81 (1H, s), 8.10–8.30 (1H, br s).

Description 45

5-Chloro-6-methylindoline (D45)

5-Chloro-6-methylindole (D44) was reduced in the usual way with sodium cyanoborohydride in glacial acetic acid to give the title compound (D45) (0.61, 94%).

NMR (CDCl$_3$) δ: 2.22 (3H, s), 2.95 (2H, t, J=8), 3.51 (2H, t, J=8), 3.60–3.75 (1H, br s), 6.51 (1H, s), 7.03 (1H, s).

Description 46

N-Acetyl-5-(N,N-dimethylamino)indoline (D46)

A mixture of N-Acetyl-5-nitroindoline (1 g, 4.9 mmol), aqueous formaldehyde (37%) (1.1 ml) and 10% palladium on carbon (0.1 g) in ethanol (18 ml) was hydrogenated at 45 psi overnight. Filtration through celite, followed by evaporation of the solvent under reduced pressure afforded the title compound (D46) as a white solid (0.96 g, 97%).

H NMR (CDCl$_3$) δ: 2.2 (3H, s, N-Ac), 2.91 (6H, s, NMe$_2$), 3.18 (2H, t), 4.04 (2H, t), 6.6 (2H, m), 8.09 (1H, d).

Description 47

6-Chloro-5-methylthioindole and 4-chloro-5-methylthioindole

3-Chloro-4-methylthioaniline (Lauterbach et al, patent Ger. Offen. 1, 141, 183) was converted to a 1:1 mixture of the title compounds by the method developed by Sundberg (J. Org. Chem., 1984, 49, 249) in an overall yield of 34%. The isomers were separated by chromatography on silica-gel using 15% diethylether in petroleum ether (40°–60°) to give in order of elution the 6-chloro isomer and the 4-chloro isomer.

6-Chloro-5-methylthioindole: NMR (CDCl$_3$) δ: 2.50 (3H, s), 6.50 (1H, m), 7.18 (1H, m), 7.47 (1H, s), 7.57 (1H, s), 8.12 (1H, b).

4-chloro-5-methylthioindole: NMR (CDCl$_3$) δ: 2.51 (3H, s), 6.62 (1H, m), 7.20–7.30 (3H, m), 8.24 (1H, b).

Description 48

6-Chloro-5-methylthioindoline (D48)

6-Chloro-5-methylthioindole (D47) (0.72 g, 3.65 mmol) was treated with sodium cyanoborohydride as in the method of Description 10 to give the title compound (0.72 g, 98%) as a pale yellow oil.

NMR (CDCl$_3$) δ: 2.40 (3H, s), 3.00 (2H, t, J=8), 3.59 (2H, t, J=8), 3.81 (1H, b), 6.66 (1H, s), 7.13.(1H, s).

Description 49

4-Chloro-5-methylthioindoline (D49)

4-Chloro-5-methylthioindole (D47) (0.89 g, 4.49mmol) was treated with sodium cyanoborohydride according to the procedure of Description 10 to afford the title compound (0.90 g, 100%) as a pale yellow oil.

NMR (CDCl$_3$) δ: 2.40 (3H, s), 3.10 (2H, t, J=8), 3.64 (1H, t, J=8), 3.88 (1H, b), 6.48 (1H, d, J=7), 7.09 (1H, d, J=7).

Description 50

5-Bromoindoline (D50)

5-Bromoindole (0.7 g, 3.6 mmol) was treated with sodium cyanoborohydride as in the method of Description 10 to yield the title compound (0.5 g, 71%).

NMR (D$_6$-DMSO) δ: 2.91 (2H, t, J=8), 3.40 (2H, t, J=8), 5.64 (1H, s), 6.42 (1H, d, J=8), 7.02 (1H, d, J=8), 7.13 (1H, s).

Description 51

6-Chloro-5-ethylindole and 4-chloro-5-ethylindole

3-Chloro-4-ethylaniline (J. P. Lampooy et al, J. Med. Chem, 1973, 16, 765) was converted to a 2:1 mixture of the title compounds by the method developed by Sundberg (J. Org. Chem., 1984, 49, 249) in an overall yield of 21%. Fractional crystallisation from petroleum ether gave the 6-chloro isomer (0.72 g). The mother liquors were concentrated to afford a mixture of the title compounds.

6-chloro-5-ethylindole: NMR (CDCl$_3$) δ: 1.30 (3H, t, J=8), 2.83 (2H, q, J=8), 6.48 (1H, m), 7.17 (1H, m), 7.41 (1H, s), 7.48 (1H, s), 8.04 (1H, b)

4-Chloro-5-ethylindole—(as component of a mixture): NMR (CDCl$_3$) δ: 1.31 (3H, t, J=8), 2.83 (2H, J=8), 6.62 (1H, m), 7.10–7.20 (3H, m), 8.10 (1H, b).

Description 52

6-Chloro-5-ethylindoline (D52)

6-Chloro-5-ethylindole (D51) (0.62 g, 3.46 mmol) was treated with sodium cyanoborohydride as in the method of Description 10 to give the title compound (0.485 g, 77%) as a yellow oil.

NMR (CDCl$_3$) δ: 1.17 (3H, t, J=8), 2.62 (2H, q, J=8), 2.96 (2H, t, J=8), 3.53 (2H, t, J=8), 3.72 (1H, b), 6.60 (1H, s), 6.95 (1H, s).

Description 53

6-Chloro-5-propylindole and 4-Chloro-5-propylindole

3-Chloro-propylaniline (prepared according to general procedure described by J. P. Lampooy et al, J. Med. Chem, 1973, 16, 765) was converted to a 7:5 mixture of the title compounds by the method developed by Sundberg (J. Org. Chem., 1984, 49, 249) in an overall yield of 14%. The isomers were separated by chromatography on silica-gel using 5% ethyl acetate in petroleum ether (60°–80° C.) to give in order of elution the 6-chloro isomer and the 4-chloro isomer.

6-Chloro-5-propylindole: NMR (CDCl$_3$) δ: 1.00 (3H, t, J=8), 1.68 (2H, m, J=8), 2.78 (2H, t, J=8), 6.47 (1H, m), 7.16 (1H, m), 7.39 (1H, s),7.45 (1H, s), 8.04 (1H, b).

4Chloro-5-propylindole

NMR (CDCl$_3$) δ: 1.03 (3H, t, J=8), 1.69 (2H, m, J=8), 2.79 (2H, t, J=8), 6.63 (1H, m), 7.12–7.25 (3H, m), 8.20 (1H, b).

Description 54

6-Chloro-5-propylindoline (D54)

6-chloro-5-propylindole (D53) (0.063 g, 0.33 mmol) was treated with sodium cyanoborohydride as in the method of Description 10 to give the title compound (0.06 g, 94%) as a yellow oil.

NMR (CDCl$_3$) δ: 0.95 (3H, t, J=8), 1.60 (2H, m, J=8), 2.58 (2H, t, J=8), 3.00 (2H, t, J=8), 3.55 (2H, t, J=8), 6.61 (1H, s), 6.93 (1H, s).

Description 55

6-Chloro-5-tert-butylindole and 4-Chloro-5-tert-butylindole

3-Chloro-4tert-butylaniline (prepared by the general procedure described by J. P. Lampooy et al, J. Med. Chem, 1973, 16, 765) was converted to a 5:4 mixture of the title compounds by the method developed by Sundberg (J. Org. Chem., 1984, 49, 249) in an overall yield of 37%. The isomers were separated by column chromatography on silica gel using 5% ethylacetate in petroleum ether (60°–80° C.) to give in order to elution the 6-Chloro isomer and the 4-Chloro isomer.

6-Chloro-5-tert-butylindole: NMR (CDCl$_3$) δ: 1.54 (9H, s), 6.50 (1H, m), 7.17 (1H, m), 7.41 (1H, s), 7.69 (1H, s), 8.02 (1H, b).

4-Chloro-5-tert-butylindole: NMR (CDCl$_3$) δ: 1.55 (9H, s), 6.70 (1H, m), 7.15–7.28 (3H, m).

Description 56

6-Chloro-5-tert-butylindoline (D56)

6-Chloro-5-tert-butylindole (D55) (0.29 g, 1.40 mmol) was treated with sodium cyanoborohydride as in the method of Description 10 to give the title compound (0.21 g, 72%) as a yellow oil.

NMR (CDCl$_3$) δ: 1.38 (9H, s), 2.89 (2H, t, J=8), 3.46 (2H, t, J=8), 3.60 (1H, b), 6.53 (1H, s), 7.09 (1H, s).

Description 57

4-Chloro-5-tert-butylindoline (D57)

4-Chloro-5-tert-butylindole (D56) (0.63 g, 3.06 mmol) was treated with sodium cyanoborohydride as in the method of Description 10 to give the title compound (0.5 g, 79%) as a yellow oil.

NMR (CDCl$_3$) δ: 1.44 (9H, s), 3.09 (2H, t, J=8), 3.58 (2H, b, J=8), 3.76 (1H, b), 6.47 (1H, d), 7.07 (1H, d).

Description 58

6-Chloro-5-isopropylindole and 4-Chloro-5-isopropylindole

3-Chloro-4-isopropylaniline (prepared by general procedure described by J. P. Lampooy et al, J. Med. Chem, 1973, 16, 765) was converted to a 7:6 mixture of the title compounds by the method developed by Sundberg (J. Org. Chem., 1984, 49, 249) in an overall yield of 51%. Fractional crystallisation from petroleum ether gave pure 6-chloro isomer (1.27 g) and the remainder as a mixture.

6-Chloro-5-isopropylindole: NMR (CDCl$_3$) δ: 1.31 (6H, d, J=8), 3.43 (1H, m), 6.48 (1H, m), 7.13 (1H,m), 7.37 (1H, s), 7.54 (1H, s), 7.98 (1H, b).

4-Chloro-5-isopropylindole—(as component of mixture): NMR (CDCl$_3$) δ: 1.29 (6H, d, J=8), 3.58 (1H, m), 6.63 (1H, m), 7.08–7.20 (3H, m), 8.02 (1H, b).

Description 59

6-Chloro-5-isopropylindoline (D59)

6-Chloro-5-isopropylindole (D58) (0.5 g, 2.60 mmol) was treated with sodium cyanoborohydride as in the method of Description 10 to give the title compound (0.4 g, 79%) as a yellow oil.

NMR (CDCl$_3$) δ: 1.19 (6H, d, J=8), 2.96 (2H, t, J=8), 3.30 (1H, m), 3.52 (2H, t, J=8), 3.65 (1H, b), 6.57 (1H, s), 7.02 (1H, s).

Description 60

1-Acetyl-6-chloro-5-iodoindoline (D60)

1-Acetyl-6-chloroindoline (0.3 g, 1.53 mmol) and iodine monochloride (2.48 g, 15.3 mmol) in acetic acid (25 ml) were heated under reflux for 48 hours. After cooling the mixture was partitioned between ethyl acetate and 10% aqueous NaOH. The organic extract was washed with aqueous Na$_2$SO$_3$ dried (Na$_2$SO$_4$) & evaporated to dryness under reduced pressure. Chromatography on silica gel using dichloromethane afforded the title compound (0.19 g, 39%).

NMR (CDCl$_3$) δ: 2.20 (3H, s), 3.13 (2H, t, J=8), 4.08 (2H, t, J=8), 7.59 (1H, s), 8.32 (1H, s).

Description 61

1-Acetyl-6-chloro-5-vinylindoline (D61)

1-Acetyl-6-chloro-5-iodoindoline (D60) (0.19 g, 0.6 mmol) was treated with vinyl tributyltin as in the method developed by Stille (A. M. Echavarren and J. K. Stille, J. Am. Chem. Soc., 1987, 109, 5478) to give the title compound (0.13 g) as a brown oil which was used without further purification.

NMR (CDCl$_3$) δ: 2.20 (3H, s), 3.13 (2H, t, J=8), 4.09 (2H, b, J=8), 5.27 (1H, d, J=10), 5.62 (1H, d, J=15), 7.36 (1H, s), 8.20 (1H, s).

Description 62

6-Chloro-5-vinylindoline (D62)

1-Acetylchloro-5-vinylindoline (D61) (0.13 g), and 10% aqueous NaOH (5 ml) were heated at reflux in ethanol (20 ml) for 2.5 hours, cooled and treated with an excess of saturated aqueous NH$_4$Cl. The mixture was partitioned between ethyl acetate and brine. The organic extracts were dried (Na$_2$SO$_4$) and evaporated to dryness under reduced pressure affording the title compound as a brown oil (0.13 g) which was used without further purification.

NMR (CDCl$_3$) δ: 3.02 (2H, t, J=8), 3.60 (2H, t, J=8), 5.14 (1H, d, J=11), 5.55 (1H, d, J=15), 6.59 (1H, s), 7.34 (1H, s).

Description 63

6-Chloro-5-ethylthioindole and 4-Chloro-5-ethylthioindole

3-Chloro-4-ethylthioaniline (Lauterbach et al, patent Ger. Offen. 1, 141, 183) was converted to a 5:3 mixture of the title compounds by the method developed by Sundberg (J. Org. Chem., 1984, 49, 249) in an overall yield of 11%. The isomers were separated by chromatography on silica gel using 0–10% ethyl acetate in petroleum ether (60°–80° C.) to give in order of elution the 6-chloro isomer and the 4-chloro isomer.

6-Chloro-5-ethylthioindole: NMR (CDCl$_3$) δ: 1.29 (3H, t, J=7), 2.93 (2H, q, J=7), 6.47 (1H, m), 7.15 (1H, m), 7.43 (1H, s), 7.71 (1H, s), 8.13 (1H, b).

4-Chloro-5-ethylthioindole: NMR (CDCl$_3$) δ: 1.30 (3H, t, J=7), 2.94 (2H, q, J=7), 6.67 (1H, m), 7.18–7.28 (3H, m), 8.30 (1H, b).

Description 64

6-Chloro-5-ethylthioindoline (D64)

6-Chloro-5-ethylthioindole (D63) (0.35 g, 1.67 mmol) was treated with sodium cyanoborohydride as in the method of Description 10 to give the title compound (0.18 g, 57%) as a yellow oil.

NMR (CDCl$_3$) δ: 1.24 (3H, t, J=7), 2.83 (2H, q, J=7), 3.00 (2H, t, J=8), 3.60 (2H, t, J=8), 3.87 (1H, b), 6.68 (1H, s), 7.20 (1H, s).

Description 65

6-Chloro-5-isopropylthioindole & 4-Chloro-5-isopropylthioindole

3-Chloro-4-isopropylthioaniline (Lauterbach et al, patent Ger. Offen. 1, 141, 183) was converted to a 2:1 mixture of the title compound by the method developed by Sundberg (J. Org. Chem., 1984, 49, 249) in an overall yield of 30%. The isomers were separated by chromatography on silica gel using 10–40% diethyl ether in petroleum ether (60°–80° C.) to give in order of elution the 6-chloro isomer and the 4-chloro isomer.

6-Chloro-5-isopropylthioindole: NMR (CDCl$_3$) δ: 1.28 (6H, d, J=7), 3.43 (1H, m, J=7), 6.51 (1H, m), 7.18 (1H, m), 7.48 (1H, s), 7.83 (1H, s), 8.26 (1H, b).

4-Chloro-5-isopropylthioindole: NMR (CDCl$_3$) δ: 1.29 (6H, d, J=7), 3.43 (1H, m, J=7), 6.67 (1H, m), 7.20–7.30 (3H, m), 8.32 (1H, b).

Description 66

6-Chloro-5-isopropylthioindoline (D66)

6-Chloro-5-isopropylthioindole (D65) (0.49 g, 2.16 mmol) was treated with sodium cyanoborohydride as in the method of Description 10 to give the title compound (0.35 g, 71%) as a yellow oil.

NMR (CDCl$_3$) δ: 1.24 (6H, d, J=7), 2.97 (2H, t, J=8), 3.28 (1H, m, J=7), 3.58 (2H, t, J=8), 3.90 (1H, b), 6.65 (1H, s), 7.22 (1H, s).

Description 67

2-Chloro-5-methyl-4-nitrophenol-O-trifluoromethane sulphonate (D67)

A solution of 2-chloro-5-methyl-4-nitrophenol (M. E. Flaugh, T. A. Crowell, J. A. Clemens, B. D. Sawyer, *J. Med. Chem.*, 1979, 22, 63.) (10.2 g, 50 mmol) in pyridine (50 ml) was treated at 0° C. with triflic anhydride (9.1 ml, 15.5 g, 55 mmol). The reaction mixture was warmed to room temperature over 2 h, then added to ether and washed with 1M aqueous hydrochloric acid (3×), half-saturated brine (3×), brine and the ether solution dried (Na$_2$SO$_4$) and evaporated. Chromatography on silica eluting with 0–20% ethyl acetate in 40/60 petroleum ether afforded the product as a yellow crystalline solid (12.0 g, 75%)

NMR (CDCL$_3$) δ: 2.65 (3H, s), 7.40 (1H, s), and 8.20 (1H, s).

Description 68

2-Chloro-5-methyl-4-nitrostyrene (D68)

The title compound (0.4 g, 84%) was prepared by palladium (0) catalysed coupling of 2-chloro-5-methyl-4-nitrophenol-O-trifluoromethane sulphonate and vinyltributyl tin, according to the method of Stille.

NMR (CDCl$_3$) δ: 2.60 (3H, s), 5.55 (1H, d, J=12), 5.90 (1H, d, J=16), 7.10 (1H, dd, J=12, 16), 7.5 (1H, s), 8.05 (1H, s).

M$^+$ 197 m/e C$_9$H$_8$ClNO$_2$ requires 197

Description 69

2-Chloro-5-methyl-4-nitrobenzaldehyde (D69)

A solution of 2-chloro-5-methyl-4-nitrostyrene (2.2 g, 11.1 mmol) in dichloromethane (100 ml) was subjected to ozonolysis (−78° C., 1 h) followed by quenching of the intermediate ozonide with triphenyl phosphine (3.05 g, 11.6 mmol). Chromatography of the crude mixture on silica eluting with 0–10% ethyl acetate in 60/80 pet ether afforded the product as a yellow crystalline solid (1.72 g, 77%).

NMR (CDCl$_3$) δ: 2.60 (3H, s), 7.90 (1H, s), 8.05 (1H, s), 10.50 (1H, s).

Description 70

2-Chloro-5-methyl-4-nitrobenzoic Acid (D70)

A solution of 2-chloro-5-methyl-4-nitrobenzaldehyde (1.72 g, 8.6 mmol) in acetic acid (20 ml) at 80° C. was treated with sodium perborate (2.64 g, 17.2 mmol). After 0.5 h a further portion of sodium perborate (1.32 g, 8.6 mmol) was added. After 0.25 h the reaction mixture was added to ethyl acetate—half saturated brine, and the organic extract dried (Na$_2$SO$_4$) and evaporated, affording the title product as a white solid (1.43 g, 77%).

NMR (DMSO) δ: 2.50 (3H, s), 7.90 (1H, s), 8.15 (1H, s).

Description 71

Methyl-6-chloroindole-5-carboxylate (D71)

This was prepared (0.56 g, 40%) from 2-chloro-5-methyl-4-nitrobenzoic acid by the Somei variation (Somei, M; Karasawa, Y; Shoda, T; Kaneko, C; *Chem. Pharm. Bull.* 1981, 29 (1), 249) of the Leimgruber indole synthesis.

NMR (CDCl$_3$) δ: 3.95 (3H, s), 6.55 (1H, m), 7.25 1H, m), 7.45 (1H, s), 8.20 (1H, s), 8.80 (1H, b s).

Description 72

Methyl-6-chloroindoline-5-carboxylate (D72)

A solution of methyl-6-chloroindole-5-carboxylate (0.73 g, 3.5 mmol) in acetic acid (16 ml) was treated with sodium cyanoborohydride (2.07 g, 32.7 mmol). After 4 h the reaction mixture was partitioned between ethyl acetate—10% aqueous sodium hydroxide. The organic extract was dried (Na$_2$SO$_4$) and evaporated affording a brown oil (0.6 g). Chromatography on silica eluting with 0.2% methanol in dichloromethane afforded the title compound as a white solid (0.19 g, 26%)

NMR (CDCl$_3$) δ: 3.00 (2H, t, J=8), 3.65 (2H, t, J=8), 3.85 (3H, s), 6.60 (1H, s), 7.65 (1H, s).

Description 73

6-Chloro-5-iodoindole (D73)

A mixture of 6-chloro-5-iodoindole and 4-chloro-5-iodoindole was prepared from 3-chloro-4-iodoaniline by the method of Sundberg. Chromatography and recrystallisation afforded the title compound (32 g, 6% from the staring aniline).

NMR (CDCl$_3$) δ: 6.45 (1H,m), 7.15 (1H, m), 7.55 (1H, s), 8.10 (1H, s).

Description 74

6-Chloro-5-iodoindoline (D74)

The title compound was prepared from the corresponding indole (D73) by reduction with sodium cyanoborohydride in acetic acid, giving the product as a brown oil (0.28 g, 85%).

NMR (CDCl3), 3.00 (2H, t, J=8), 3.60 (2H, t, J=8), 3.8 (1H, b s), 6.70 (1H, s), 7.45 (1H, s).

Description 75

6-Bromoindole (D75)

4-Bromo-2-nitrotoluene was converted to the title compound by the method of Leimgruber (A. D. Batcho, W. Leimgruber, Organic Synthesis Collective Volume (VIII), P34).

NMR (CDCl$_3$) δ: 6.5 (1H, m), 7.1 (1H, dd, J=1,7), 7.20 (1H, m), 7.40 (1H, s), 7.55 (1H, d, J=7), 8.16 (1H, b s).

Description 76

6-Bromoindoline (D76)

6-Bromoindole (D75) was reduced with sodium cyanoborohydride as in the method of Description 10 to yield the title compound (D76).

NMR (CDCl$_3$) δ: 2.96 (2H, t, J=8), 3.57 (2H, t, J=8), 3.80 (1H, bs), 6.70 (1H, d, J=1), 6.77 (1H, dd, J=1, 7), 6.94 (1H, d, J=7).

Description 77

Di-[5-(6-bromoindolinyl)]disulphide (D77)

Bromine (1.44 ml, 27.9 mmol) in methanol (50 ml) was added dropwise over 15 min to a mixture of 6-bromoindoline (D76) (5.16 g, 26.06 mmol) and potassium thiocyanate (5.06 g, 52.16 mmol) in methanol (100 ml) at −5°–0° C. The mixture was warmed to room temperature and stirred for 1.5 hr then evaporated to dryness. The solid residue was treated with methanol (100 ml), water (100 ml) and 10% aqueous NaOH (100 ml) at room temperature for 4 hrs then partially evaporated under reduced pressure. Brine (100 ml) was added and the mixture was extracted with ethyl acetate (3×250 ml). The combined organic extracts were washed with brine then dried (Na$_2$SO$_4$) and evaporated to an oil which was chromatographed on silica using 30% ethyl acetate in petroleum ether as eluant to afford the title compound (3.68 g, 63%) as a yellow solid.

NMR (CDCl$_3$) δ: 2.88 (2H, t, J=8), 3.49 (2H, t, J=8), 6.18 (1H, bs), 6.68 (1H, s), 7.13 (1H, s).

Description 78

Di-[5-(1-acetyl-6-bromoindolinyl)]disulphide (D78)

Acetic anhydride (1.52 ml, 16.1 mmol) in dichloromethane (20 ml) was added dropwise over 10 min to a mixture of the disulphide (D77) (3.68 g, 8.03 mmol) and triethylamine (3 ml, 21.5 mmol) in dichloromethane (100 ml) at 0° C. The mixture was allowed to warm to room temperature and after 2 hr poured into 2.5M aqueous HCl (150 ml). The aqueous was further extracted with dichloromethane (100 ml) and the organic layers were combined, dried (Na$_2$SO$_4$) and evaporated to a solid residue which was recrystallised from ethyl acetate to give the title compound (2.77 g, 63%) as an off-white solid.

NMR (CDCl$_3$) δ: 2.20 (3H, s), 3.12 (2H, t, J=8), 4.06 (2H, t, J=8), 7.39 (1H, s), 8.42 (1H, s).

Description 79

1-Acetyl-6-bromo-5-mercaptoindoline (D79)

A mixture of the diacetyl disulphide (D78) (1.5 g, 2.76 mmol), triphenylphosphine (1.05 g, 4 mmol) and conc. HCl (2 drops) in dioxan (15 ml) and water (3 ml) was heated at reflux for 3 hr then cooled and evaporated. The residue was partitioned between dichloromethane (100 ml) and 1% aqueous NaOH (150 ml). The aqueous phase was extracted with another portion of dichloromethane (100 ml) then carefully acidified with 5M aqueous HCl and extracted with dichloromethane (3×100 ml). The combined organics were dried (Na$_2$SO$_4$) and evaporated to afford the title compound (0.9 g, 60%) as a white solid.

NMR (CDCl$_3$) δ: 2.20 (3H, s), 3.11 (2H, t, J=8), 3.90 (1H, s), 4.04 (2H, t, J=8), 7.15 (1H, s), 8.41 (1H, s).

Description 80

1-Acetyl-6-bromo-5-propylthioindoline (D79)

A mixture of the thiol (D79) (0.1 g, 0.37 mmol), anhydrous K$_2$CO$_3$ (0.056 g, 0.41 mmol) and 1-iodopropane (0.04 ml, 0.41 mmol) in dry DMSO (10 ml) was heated at 90° C. for 0.5 hr. The reaction mixture was cooled, poured into water (100 ml) and extracted with dichloromethane (3×75 ml). The combined organics were washed with water (150 ml), dried (Na$_2$SO$_4$) and evaporated to yield the title compound (0.12 g, 100%) as an off-white solid.

NMR (CDCl$_3$) δ: 0.98 (3H, t, J=7), 1.61 (2H, m, J=7), 2.13 (3H, s),2.79 (2H, t, J=7), 3.07 (2H, t, J=8), 4.00 (2H, t, J=8); 7.05 (1H, s), 8.39 ((H, s).

Description 81

1-Acetyl-6-bromo-5-ethylthioindoline (D81)

The thiol (D79) (0.35 g, 1.29 mmol) was treated with K$_2$CO$_3$ (0.20 g, 1.45 mmol) and iodoethane (0.31 ml, 3.88 mmol) in DMSO (15 ml) at the 50° C. as in the method of Description 80 to afford the title compound (0.39 g, 100%) as a pale yellow solid.

NMR (CDCl$_3$) δ: 1.25 (3H, t, J=7), 2.12 (3H, s), 2.82 (2H, q, J=7), 3.06 (2H, t, J=8), 3.98 (2H, t, J=8), 7.06 (1H, s), 8.37 (1H, s).

Description 82

1-Acetyl-6-bromo-5-methylthioindoline (D82)

The thiol (D79) (0.35 g, 1.29 mmol) was treated with K$_2$CO$_3$ (0.20 g, 1.45 mmol) and iodomethane (0.24 ml, 3.85 mmol) in DMSO (15 ml) at 50° C. as in the method of Description 80 to afford the title compound (0.34 g, 92%) as an off-white solid.

NMR (CDCl$_3$) δ: 2.12 (3H, s), 2.37 (3H, s), 3.08 (2H, t, J=8), 3.99 (2H, t, J=8), 6.92 (1H, s), 8.35 (1H, s).

Description 83

6-Bromo-5-propylthioindoline (D83)

The acetyl indoline (D80) (0.12 g, 0.37 mmol) was treated with NaOH (1.11 g, 27.75 mmol) in water (7 ml) and ethanol (4 ml) at reflux for 3 hrs. The reaction mixture was cooled, diluted with water (50 ml) and extracted with dichloromethane (3×50 ml). The combined extracts were dried (Na$_2$SO$_4$) and evaporated to give the title compound (0.096 g, 96%) as an oil.

NMR (CDCl$_3$) δ: 1.01 (3H, t, J=7), 1.61 (2H, m, J=7), 2.78 (2H, t, J=7), 2.98 (2H, t, J=8), 3.59 (2H, t, J=8), 3.82 (1H, bs), 6.86 (1H, s), 7.21 (1H, s).

Description 84

6-Bromo-5-ethylthioindoline (D84)

The acetyl indoline (D82) (0.38 g, 1.27 mmol) was treated with NaOH (1.4 g, 35 mmol) in water (9 ml) and ethanol (5 ml) as in the method of Description 83 to afford the title compound (0.29 g, 88%) as a yellow oil.

NMR (CDCl$_3$) δ: 1.26 (3H, t, J=7), 2.82 (2H, q, J=7), 2.98 (2H, t, J=8), 3.59 (2H, t, J=8), 3.83 (1H, bs), 6.86 (1H, s), 7.22 (1H, s).

Description 85

6-Bromo-5-methylthioindoline (D85)

The acetyl indoline (D82) (0.33 g, 1.15 mmol) was treated with NaOH (1.5 g, 37.5 mmol) in water (9 ml) and ethanol (5 ml) as in the method of Description 83 to afford the title compound (0.26 g, 92%) as an oil.

NMR (CDCl$_3$) δ: 2.40 (3H, s), 2.98 (2H, t, J=8), 3.58 (2H, t, J=8), 3.80 (1H, bs), 6.84 (1H, s), 7.12 (1H, s).

Example 1

5-Ethylthio-1-(3-pyridylcarbamoyl)indoline (E1)

A solution of nicotinic acid azide (85 mg, 0.56 mmol) in toluene (4 ml) was heated under reflux for 1.75 h, then cooled. A solution of indoline D7 (0.10 g, 0.56 mmol) in dichloromethane (4 ml) was added, and the mixture was stirred overnight at room temperature. The mixture was then partially evaporated in vacuo and a little petrol was added. The resulting precipitate was filtered off and recrystallised, firstly from dichloromethane/petrol and then from ethanol/water to give the title compound (0.138 g, 82%) mp 150°–151° C.

NMR (D$_6$ DMSO) δ: 1.18 (3H, t, J=7), 2.88 (2H, q, J=7), 3.18 (2H, t, J=8), 4.14 (2H, t, J=8), 7.14 (1H, d, J=8), 7.22 (1H, s), 7.32 (1H, dd, J=7,5), 7.81 (1H, d, J=8), 7.97 (1H, d, J=7), 8.22 (1H, d, J=5), 8.73 (2H, s) Found: C, 63.94; H, 5.71; N, 13.98% C$_{16}$H$_{17}$N$_5$OS requires: C, 64.19; H, 5.72; N, 14.03%

Example 2

6-Chloro-5-methyl-1-(3-pyridycarbamoyl)indoline (E2)

Nicotinoyl azide (0.111 g, 0.75 mmol) was heated at reflux under Ar in dry toluene (8 ml) for 45 min, and cooled to ambient temperature. This solution was filtered, through a small cotton-wool plug, into a stirred solution of 6-chloro-5-methylindoline (D10) (0.105 g, 0.63 mmol), with immediate precipitation. The suspension was stirred for 30 min, and the solid was filtered off and dried in vacuo at 60° C., giving the title compound (0.113 g, 62%) as a white powder, m.p. 221°–221½° C.

NMR (DMSO-D$_6$) δ: 2.25 (3H, s), 3.15 (2H, t, J=8), 4.16 (2H, t, J=8), 7.17 (1H, s), 7.33 (1H, dd, J=8, 4), 7.88 (1H, s), 7.98 (1H, dm), 8.23 (1H, dd, J=5,2), 8.75 (2H,m).

Found: C, 62.6; H, 5.0; N, 14.6% C$_9$H$_{10}$ClN requires: C, 62.6; H, 4.9; N, 14.6% Found: M$^+$ 287, 289, C$_9$H$_{10}$ClN requires: 287, 289

Example 3

6-Chloro-5-methyl-1-(3-pyridylcarbamoyl)indoline and 4-chloro-5-methyl-1-(3-pyridylcarbamoyl)indoline (E3)

These were prepared, as a mixture, from the mixture of 6-chloro-5-methylindoline and 4-chloro-5-methylindoline (0.47 g, 2.8 mmol), prepared as described in Description 11, following the procedure of Example 2. This gave a mixture of the title compounds (0.66 g, 81%), in approximate proportions 2:1.

4-chloroisomer (as component of mixture), NMR (DMSO-D$_6$) δ: 2.26 (3H, s), 3.17 (2H, t, J=8), 4.19 (2H, t, J=8), 7.11 (1H, d, J=8), 7.32 (1H, dd, J=8, 4), 7.71 (1H, d, J=8), 7.98 (1H, m), 8.23 (1H, m), 8.74 (2H, m)

Mixture: Found: C, 62.8; H, 5.0; N, 14.5% C$_9$H$_{10}$ClN requires C, 62.6; H. 4.9; N, 14.6% Found: M$^+$ 287, 289, C$_9$H$_{10}$ClN requires 287, 289.

Example 4

5-(N,N-Dimethylamino)-1-(3-pyridylcarbamoyl) indoline (E4)

5-(N,N-dimethylamino)indoline (D13) (0.29 g, 1.79 mmol) was added to solution of 3-pyridylisocyanate derived from nicotinoyl azide (0.52 g, 1.2 eq) heated at reflux in dry toluene for 1.5 h. The solution was allowed to stand overnight evaporated under reduced pressure and purified by column chromatography (SiO$_2$, CHCl$_3$/MeOH 2–5%) to afford a pale blue oil which on trituration with Et$_2$O afforded a pale blue solid (550 mg, 99%).

NMR (D$_6$ DMSO) δ: 2.82 (6H, s), 3.14 (2H, t), 4.08 (2H, t), 6.53 (1H, dd), 6.68 (1H, d), 7.70 (1H, d), 7.98 (1H, dd), 8.20 (1H, m), 8.58 (1H, s), 8.72 (1H, d)

Found: C, 65.56; H, 6.30; N, 19.25% C$_{16}$H$_{18}$N$_4$O ⅔H$_2$O requires C, 65.31; H, 6.35; N, 19.05% Found: M$^+$ 282, C$_{16}$H$_{18}$N$_4$O requires 282

Example 5

5-Iodo-1-(3-pyridylcarbamoyl)indoline (E5)

The title compound was prepared in 73% from nicotinic acid azide and 5-iodoindoline using a procedure similar to that for Example 1, m.p. 210°–215° C.

NMR (D$_6$-DMSO) δ 3.13 (2H, t, J 8), 4.08 (2H, t, J 8), 7.27 (1H, m), 7.40 (1H, m), 7.48 (1H, s), 7.63 (1H, d, J 8), 7.91 (1H, m), 8.17 (1H, m), 8.68 (2H, m).

Found: C, 46.38; H, 3.49; N, 11.45% C$_{14}$H$_{12}$N$_3$O I requires C, 46.05; H, 3.31; N, 11.51% Found: M$^+$ 365, C$_{14}$H$_{12}$N$_3$OI requires 365

Example 6

5-Nitro-1-(3-pyridylcarbamoyl)indoline Hydrochloride

This material was prepared from nicotinoyl azide (0.43 g, 2.9 mmol) and 5-nitroindoline (0.38 g, 2.3 mmol), and conversion of the precipitated urea to the salt using excess HCl in ether, following the procedure of Example 2. This gave the title compound (0.64 g, 76%) as a light yellow powder, m.p. 244°–7° C. (dec.).

NMR (DMSO-d$_6$) δ: 3.32 (2H, t, J=8), 4.35 (2H, t, J=8), 7.8–8.2 (4H, m), 8.5–8.65 (2H, m), 9.14 (1H, d, J=2), 9.78 (1H, s).

M.S. (C.I.) (M/Z) [M+H]$^+$=285. C$_{14}$H$_{12}$N$_4$O$_3$. HCl requires [M+H]$^+$=285.

Example 7

5-Methylthio-1-(3-pyridylcarbamoyl)indoline (E7)

A solution of nicotinoyl azide (0.3 g, 2.0 mmol) in toluene (14 ml) was heated under reflux for 1.25 h. After cooling, a solution of indoline (D19, 0.32 g, 1.9 mmol) was added and the mixture was stirred at room temperature overnight. The precipitate was filtered off, washed with petrol and dried. Recrystallisation from 50% aqueous ethanol gave the title compound (0.43 g, 77%), mp. 160°–162° C.

NMR (d$_6$-DMSO) δ 2.44 (3H, s), 3.18 (2H, t, J=8), 4.15 (2H, t, J=8), 7.08 (1H, d, J=7), 7.19 (1H, s), 7.33 (1H, dd, J=7,5), 7.82 (1H, d, J=7), 7.98 (1H, d, J=7), 8.22 (1H, d, J=5), 8.74(1H, s).

Found: C, 63.03; H, 5.37; N, 14.58% C$_{15}$H$_{15}$N$_3$OS requires C, 63.13; H, 5.30; N, 14.72%

Example 8

5-(2-Propyl)-1-(3-pyridylcarbamoyl)indoline (E8)

The title compound was prepared from D18 according to the procedure of example 2. In this case evaporation of dichloromethane from the final mixture was required to give a precipitate which was filtered off, washed with petrol and dried to give the product (0.485 g, 45%), m.p. 163°–165° C.

NMR (D$_6$-DMSO) δ: 1.18 (6H, d, J=7), 2.83 (1H, m, J=7), 3.18 (2H, t, J=8), 4.13 (2H, t, J=8), 7.00 (1H, d, J=7), 7.10 (1H, s), 7.32 (1H, dd, J=7,5), 7.77 (1H, d, J=7), 7.99 (1H, dm, J=7), 8.22 (1H, d, J=5), 8.69 (1H, s), 8.74 (1H, d, J=2).

Found: C, 72.14; H, 6.75; N, 15.12% C$_{17}$H$_{19}$N$_3$O requires C, 72.57; H, 6.81; N, 14.93%

Example 9

4,6-Dichloro-5-methyl-1-(3-pyridylcarbamoyl) indoline (E9)

The title compound was prepared from D22 and nicotinoyl azide according to Example 2. Amount Prep=1 g (27%) (recryst. DCM/EtOH) Mpt—234° C.–235° C.

NMR (250 MHz, DMSO d$^6$) δ$_H$: 8.82 (s, 1H, Ar), 8.7 (m, 1H, Ar), 8.25 (d, 1H, Ar, J=5.2 Hz), 7.95 (m, 1H, Ar), 7.32 (m, 1H, Ar), 4.20 (t, 2H, J=8Hz), 3.17 (t, 2H, J=8Hz), 2.32 (s, 3H, CH$_3$)

| Analysis: | | |
|---|---|---|
| | Required % | Found % |
| C | 55.92 | 55.89 |
| H | 4.07 | 4.16 |
| N | 13.04 | 13.16 |

M$^+$=322, C$_{15}$H$_{13}$N$_3$Cl$_2$O requires 322

Example 10

6-Fluoro-5-methyl-1-(3-pyridylcarbamoyl)indoline (E10)

The title compound was prepared from 6-fluoro-5-methylindoline (D24) and nicotinoyl azide using a procedure similar to that in Example 2. Recrystallisation from ethanol afforded the pure product, m.p. 203°–205° C.

NMR (D$_6$-DMSO) δ: 2.15 (3H, s), 3.15 (2H, t, J=9), 4.18 (2H, t, J=9), 7.08 (1H, d, J=8), 7.35 (1H, m), 7.59 (1H, d, J=8), 7.99 (1H, m), 8.23 (1H, m), 8.74 (2H, m). M$^+$ 271, C$_{15}$H$_{14}$FN$_3$O requires 271

Example 11 and Example 12

6-Iodo-5-methyl-1-(3-pyridylcarbamoyl)indoline (E11)

4-Iodo-5-methyl-1-(3-pyridylcarbamoyl)indoline (E12)

The title compounds were prepared from a mixture of 4-iodo-5-methylindoline and 6-iodo-5-methylindoline (D26) and nicotinoyl azide using a procedure similar to that in Example 2. HPLC separation furnished a pure sample of each isomer.

E11: NMR (D$_6$-DMSO) δ: 2.32 (3H, s), 3.13 (2H, t, J=9), 4.15 (2H, t, J=9), 7.19 (1H, s), 7.33 (1H, m), 7.98 (1H, m), 8.23 (1H, m), 8.34 (1H, s), 8.73 (1H, m).

E12: NMR (D$_6$-DMSO) δ: 2.33 (3H, s), 3.11 (2H, t, J=9), 4.17 (2H, t, J=9), 7.09 (1H, d, J=8), 7.34 (1H, m), 7.76 (1H, d, J=8), 7.97 (1H, m), 8.23 (1H, m), 8.71 (1H, s), 8.74 (1H, m).

Example 13 and Example 14

6-Bromo-5-methyl-1-(3-pyridylcarbamoyl)indoline (E13)

4-Bromo-5-methyl-1-(3-pyridylcarbamoyl)indoline (E14)

The title compounds were prepared from a mixture of 4bromo-5-methylindoline and 6-bromo-5-methylindoline (D28) and nicotinoyl azide using a procedure similar to Example 1, HPLC separation furnished a pure sample of each isomer.

E13: NMR (CDCl$_3$) δ: 2.34 (3H, s), 3.20 (2H, t, J=9), 4.12 (2H, t, J=9), 6.42 (1H, b s), 7.04 (1H, s), 7.27 (1H, m), 8.11 (1H, m), 8.16 (1H, s), 8.35 (1H, m), 8.50 (1H, s).

E14: NMR (CDCl$_3$) δ: 2.36 (3H, s), 3.27 (2H, t, J=9), 4.15 (2H, t, J=9), 6.45 (1H, b s), 7.09 (1H, d, J=8), 7.28 (1H, m), 7.75 (1H, d, J=8), 8.09 (1H, m), 8.32 (1H, m), 8.50 (1H, s).

Example 15

5-Phenyl-1-(3-pyridylcarbamoyl)indoline (E15)

The title compound was prepared as in the method of (Example 2) from 3-pyridyl isocyanate and 5-phenylindoline (D30) to give (E15) (0.73 g, 52%) m.p. 241°–2° C.

NMR (DMSO-d$_6$) δ: 3.25 (2H, t, J=8), 4.19 (2H, t, J=8), 7.23–7.69 (8H, m), 7.89–8.03 (2H, m), 8.09–8.13 (1H, m), 8.75–8.80 (2H, m). MH$^+$ 316, C$_{20}$H$_{17}$N$_3$O H$^+$ requires 316

Example 16

4,5-Dichloro-1-(3-pyridylcarbamoyl)indoline (E16)

The title compound was prepared as in the method of (Example 2) from 3-pyridylisocyanate and 4,5-dichloroindoline (D32) to give (E16) (0.5 g, 25%) m.p. >240° C.

NMR (DMSO-d$_6$) δ: 3.28 (2H, t, J=8), 4.21 (2H, t, J=8), 7.30–7.42 (2H, m), 7.80 (1H, d, J=8), 7.92–7.98 (1H, m), 8.20–8.24 (1H, m), 8.72 (1H, s), 8.82 (1H, s).

Example 17

6,7-Dichloro-1-(3-pyridylcarbamoyl)indoline (E17)

The title compound was prepared as in the method of (Example 2) from 3-pyridylisocyanate and 6,7-dichloroindoline (D34) to give (E17) (0.84 g, 46%) m.p. 178°–180° C.

NMR (DMSOd$_6$) δ: 3.11 (2H, t, J=8), 4.19 (2H, t, J=8), 7.21–7.35 (3H, m), 7.89–7.94 (1H, m), 8.09–8.12 (1H, m), 8.70 (1H, s), 9.68 (1H, s).

Example 18

5-Chloro-1-(3-pyridylcarbamoyl)indoline (E18)

The title compound was prepared as in the method of (Example 2) from 3-pyridylisocyanate and 5-chloroindoline (D35) to give (E18) (1.4 g, 82%) m.p. 204°–5° C.

NMR (DMSO-d$_6$) δ: 3.18 (2H, t, J=8), 4.15 (2H, t, J=8), 7.15–7.18 (1H, m), 7.25 (1H, s), 7.27–7.35 (1H, m), 7.85 (1H, d, J=8), 7.93–8.00 (1H, m), 8.19–8.24 (1H, m), 8.70–8.80 (2H, m)

Example 19

6-Chloro-1-(3-pyridylcarbamoyl)indoline (E19)

The title compound was prepared as in the method of (Example 2) from 3-pyridylisocyanate and 6-chloroindoline (D36) to give (E19) (1.54 g, 73%) m.p. 204°–5° C.

NMR (DMSO-d$_6$) δ: 3.19 (2H, t, J=8), 4.19 (2H, t, J=8), 6.93–6.99 (1H, m), 7.23 (1H, d, J=8), 7.31–7.38 (1H, m), 7.88 (1H, s), 7.94–8.02 (1H, m), 8.24 (1H, d, J=6), 8.72 (1H, s), 8.82 (1H, s).

Found: C, 61.34; H, 4.60; N, 15.38 C$_{14}$H$_{12}$N$_3$OCl requires: C, 61.43; H, 4.42; N, 15.35

Example 20

5,6-Dichloro-1-(3-pyridylcarbamoyl)indoline (E20)

The title compound was prepared as in the method of (Example 2) from 3-pyridylisocyanate and 5,6-dichloroindoline (D39) to give (E20) (1.27 g, 65%) m.p. 236°–238° C.

NMR (DMSO-d$_6$) δ: 3.18 (2H, t, J=8), 4.21 (2H, t, J=8), 7.28–7.35 (1H, m), 7.47 (1H, s), 7.92–7.99 (1H, m), 8.00 (1H, s), 8.23 (1H, d, J=6), 8.70 (1H, s), 8.83 (1H, s).

Found: C, 54.59; H, 3.81; N, 13.60 C$_{14}$H$_{11}$N$_3$OCl$_2$ requires: C, 54.57; H, 3.60; N, 13.64

Example 21

5-(3-Thienyl)-1-(3-pyridylcarbamoyl)indoline (E21)

The title compound was prepared as in the method of (Example 2) form 3-pyridylisocyanate and 5-(3-Thienyl)indoline (D41) to give (E21) (0.89 g, 56%) m.p. 215°–217° C.

NMR (DMSO-d$_6$) δ: 3.22 (2H, t, J=8), 4.19 (2H, t, J=8),7.29–7.36 (1H, m), 7.49–7.62 (4H, m), 7.73 (1H, s), 7.89 (1H, d, J=8), 7.95–8.04 (1H, m), 8.19–8.27 (1H, m), 8.73 (2H, s).

MH$^+$ 322 C$_{18}$H$_{15}$N$_3$OS.H$^+$ requires 322

Example 22

5-Trifluoromethyl-1-(3-pyridylcarbamoyl)indoline (E22)

The title compound was prepared as in the method of (Example 2) from 3-pyridylisocyanate and 5-trifluoromethylindoline (D43) to give (E22) (0.12 g, 38%) m.p. 188°–189° C.

NMR (DMSO-d$_6$) δ: 3.28 (2H, t, J=8), 4.22 (2H, t, J=8), 7.31–7.37 (1H, m), 7.47–7.57 (2H, m), 7.95–8.03 (2H, m), 8.24 (1H, d, J=6), 8.75 (1H, s), 8.90 (1H, s). MH$^+$ 308 C$_{15}$H$_{12}$N$_3$OF$_3$ H$^+$ requires 308

Example 23

5-Chloro-6-methyl-1-(3-pyridylcarbamoyl)indoline (E23)

The title compound was prepared as in the method of (Example 2) from 3-pyridylisocyanate and 5-chloro-6-methylindoline (D45) to give (E23) (0.76 g, 73%) m.p. 217°–218° C.

NMR (DMSO-d$_6$) δ: 2.27 (3H, s), 3.13 (2H, t, J=8), 4.13 (2H, t, J=8), 7.21 (1H, s), 7.29–7.37 (1H, m), 7.82 (1H, s), 7.93–7.99 (1H, m), 8.22 (1H, d, J=6), 8.73 (1H, s).

Found: C, 62.61; H, 5.02; N, 14.38 C$_{15}$H$_{14}$N$_3$OCl requires: C, 62.61; H, 4.90; N, 14.60

Example 24

6-Chloro-5-methyl-1-(2-methyl-4-quinolyl-1-carbamoyl)indoline (E24)

A solution of carbonyl diimidazole (0.41 g, 2.5 mmol) in dichloromethane (30 ml) was treated with 2-methyl-4-amino-quinoline (0.37 g, 2.4 mmol). The mixture was warmed to 30° C. for 5 minutes then stirred at room temperature for 0.5 h. Evaporation afforded a yellow solid which was dissolved in N,N-dimethylformamide (10 ml) and treated with a solution of 6chloro-5-methyl-indoline (D10) (0.36 g, 2.2 mmol) in N,N-dimethylformamide (10 ml). The mixture was heated to 100° C. for 0.75 h, cooled to room temperature then added to water with vigorous stirring. Filtration and drying afforded the crude product as a yellow solid. (0.45 g). Recrystallisation from ethanol afforded the title compound as a yellow solid (0.35 g, 46%), m.p. >230° C.

NMR (DMSO) δ: 2.25 (3H, s), 2.65 (3H, s), 3.15 (2H, m), 4.35 (2H, m), 7.20 (1H, bs), 7.55 (1H, m), 7.70 (2H, m), 7.90 (2H, m), 8.15 (1H, m), 8.85 (1H, b s). M$^+$ 351 C$_{20}$H$_{18}$ClN$_3$O requires 351

Found: C, 68.16; H, 5.34; N, 11.99 C$_{20}$H$_{18}$ClN$_3$O requires: C, 68.27; H, 5.16; N, 11.94.

Example 25

6-Chloro-5-methyl-1-(4-pyridylcarbamoyl)indoline (E25)

The title compound was prepared as a white solid from 4-aminopyridine and 6-chloro-5-methyl-indoline (D10) by the same method as for (Example 24), (0.50 g, 86%) m.p. >230° C.

NMR (DMSO) δ: 2.25 (3H, s), 3.15 (2H, t, J=8), 4.13 (2H, t, J=8), 7.20 (1H, s), 7.60 (2H, d, J=7), 7.85 (1H, s), 8.35 (2H, d, J=7), 8.90 (1H, s). M$^+$ 287 C$_{15}$H$_{14}$ClN$_3$O requires 287

Example 26

6-Chloro-5-methyl-1-(5-quinolylcarbamoyl)indoline (E26)

The title compound was prepared as a white solid from 5-aminoquinoline and 6-chloro-5-methyl-indoline (D10) by the same method as for (Example 24), (0.15 g, 21%)

NMR (DMSO) δ: 2.25 (3H, s), 3.20 (2H, t, J=8), 4.30 (2H, t, J=8), 7.20 (1H, s), 7.50–7.60 (2H, m), 7.75 (1H, t, J=7), 7.85 (1H, s), 7.95 (1H, d, J=7), 8.40 (1H, d, J=7), 8.90 (2H, m).

MH$^+$ 338 C$_{19}$H$_{16}$ClN$_3$O requires 337

Example 27

6-Chloro-5-methyl-1-(3-methyl-5-isoxazolylcarbamoyl)indoline (E27)

A solution of 3-amino-5-methyl-isoxazole (0.23 g, 2.4 mmol) in N,N-dimethylformamide (4 ml) was treated at 0° C. with sodium hydride (70 mg of 80% dispersion; 2.4 mmol). After 0.25 h the mixture was added dropwise to a solution of carbonyl diimidazole (0.41 g, 2.5 mmol) in N,N-dimethylformamide (4 ml), and after 5 mins the resulting solution was added to a solution of 6chloro-5-methyl indoline (D10) (0.36 g, 2.2 mmol) in N,N-dimethylformamide (4 ml). The mixture was heated at 100° C. for 1 h, allowed to cool to room temperature, then treated with 0.1M aqueous hydrochloric acid (30 ml). Filtration and drying afforded a brown solid (0.5 g). Recrystallisation from ethanol gave the title compound as a white solid (0.40 g, 64%) m.p. >220° C., NMR (DMSO) δ: 2.20 (3H, s), 2.30 (3H, s), 3.15 (2H, t, J=8), 4.15 (2H, t, J=8), 6.05 (1H, s), 7.20 (1H, s), 7.75 (1H, s), 10.35 (1H, s).

M⁺ 291 $C_{14}H_{14}ClN_3O_2$ requires 291 Found: C, 57.73; H, 4.98; N, 14.53 $C_{14}H_{14}ClN_3O_2$ requires C, 57.64; H, 4.84; N, 14.40

Example 28

5-(N,N-Dimethylamino)-1-(2-methyl-4-quinolinylcarbamoyl)indoline (E28)

N-Acetyl-5-(N,N-dimethylamino)indoline (D46) (1.0 g, 4.9 mmol) and conc. HCl (1 ml) were heated over a stream bath for 0.75 h, basified with solid $K_2CO_3$ and then extracted with chloroform (100 ml). The extracts were died ($Na_2SO_4$) and evaporated under reduced pressure. The residue was chromatographed on silica gel using 5–10% methanol in ethylacetate as eluent to afford 5-N,N-dimethylaminoindoline (0.69 g, 87%) which was used immediately in the next step.

Carbonyl diimidazole (1.97 g, 11 mmol) in dry dichloromethane (40 ml) was stirred as 4-aminoqunialdine (1.75 g, 11 mmol) was added to give a bright yellow precipitate. After 30 min, the suspension was evaporated to dryness and the residue dissolved in dry DMF (40 ml). The indoline (D46) (1.79 g, 11 mmol) was added followed by triethylamine (1.55 ml, 11 mmol) and the mixture was heated to 90° C. for 1 h then left overnight at room temperature. Water (70 ml) was added and the resulting precipitate filtered off and extracted with 20% MeOH/CHCl₃. These extracts were washed with aqueous $NaHCO_3$, dried ($Na_2SO_4$), evaporated to dryness under reduced pressure and purified by chromatography on silica gel using 2–10% methanol in chloroform to afford the title compound (4.18 g, 100%) as a pale yellow solid m.p. 252°–253° C.

H NMR (D₆ DMSO) δ: 2.84 (6H, s, NMe₂), 3.18 (2H, t), 3.38 (3H, s), 4.30 (2H, t), 6.54 (1H, d), 6.70 (1H, s), 7.50 (1H, t), 7.71 (3H, m), 7.89 (1H, d), 8.13 (1H, d), 8.65 (1H, NH amide).

Found: C, 72.72; H, 6.45; N, 16.24% $C_{21}H_{22}N_4O$ requires: C, 72.81; H, 6.40; N, 16.17%

Example 29

6-Chloro-5-methylthio-1-(3-pyridylcarbamoyl) indoline (E29)

6-Chloro-5-methylthioindoline (D48) (0.70 g, 3.51 mmol) was treated with 3-pyridylisocyanate as in the procedure described in Example 1. The crude product was recrystallised from ethanol/diethyl ether to give the title compound (0.91 g, 81%) as a white crystalline solid m.p. 241°–242° C.

NMR (D₆ DMSO) δ: 2.48 (3H, s), 3.22 (2H, t, J=8), 4.18 (2H, t, J=8), 7.22 (1H, s), 7.33 (1H, dd, J=9 & 5), 7.91 (1H, s), 7.98 (1H, d, J=9), 8.23 (1H, d, J=5), 8.74 (1H, m), 8.80 (1H, s).

Found: C, 56.31; H, 4.56; N, 13.11% $C_{15}H_{14}N_3OSCl$ requires: C, 56.33; H, 4.41; N, 13.14%

Example 30

4-Chloro-5-methylthio-1-(3-pyridylcarbamoyl) indoline (E30)

4-Chloro-5-methylthioindoline (D49) (0.9 g, 4.51 mmol) was treated with 3-pyridylisocyanate as in the procedure described in Example 1. The crude product was filtered-off and recrystallised from ethanol to give the title compound (1.22 g, 84%) as a white crystalline solid m.p. 237°–241° C.

NMR (D₆-DMSO) δ: 2.43 (3H, s), 3.20 (2H, t, J=8), 4.20 (2H, t, J=8), 7.14 (1H, d, J=7), 7.34 (1H, dd, J=9 & 5), 7.83 (1H, d, J=7), 8.98 (1H, d, J=7), 8.24 (1H, d, J=5), 8.73 (1H, m), 8.78 (1H, s).

Found: C, 55.86; H, 4.54; N, 13.11% $C_{15}H_{14}N_3OSCl$ requires: C, 56.33; H, 4.41; N, 13.14%

Example 31

5-Bromo-1-(3-pyridylcarbamoyl)indoline (E31)

5-Bromoindoline (D50) (0.5 g, 2.5 mmol) was treated with 3-pyridylisocyanate as in the method of Example 1. The product was filtered-off and recrystallised from methanol/water to afford the title compound (0.58 g, 72%) as a white crystalline solid m.p. 220° C.

NMR (D₆-DMSO) δ: 3.21 (2H, t, J=8), 4.18 (2H, t, J=8), 7.27–7.38 (2H, m), 7.40 (1H, s), 7.81 (1H, d, J=8), 7.97 (1H, d, J=8), 8.23 (1H, d, J=5), 8.73 (1H, m), 8.79 (1H, s).

Example 32

6-Chloro-5-ethyl-1-(3-pyridylcarbamoyl)indoline (E32)

6-Chloro-5-ethylindoline (D52) (0.42 g, 2.33 mmol) was treated with 3-pyridylisocyanate as in the procedure described in Example 1. The crude product was recrystallised from ethanol/diethyl ether to give the title compound (0.42 g, 59%) as a white crystalline solid m.p.=227° C.

NMR (D₆DMSO) δ: 1.13 (3H, t, J=8), 2.62 (2H, q, J=8), 3.17 (2H, t, J=8), 4.16 (2H, t, J=8), 7.18 (1H, s), 7.33 (1H, m), 7.87 (1H, s), 7.99 (1H, d, J=9), 8.23 (1H, d, J=5), 8.73 (1H, m), 8.79 (1H, s).

Found: C, 63.52; H, 5.43; N, 14.06% $C_{16}H_{16}H_3ClO$ requires: C, 63.68; H, 5.34; N, 13.92%

Example 33

6-Chloro-5-propyl-1-(3-pyridylcarbamoyl)indoline (E33)

6-Chloro-5-propylindoline (D54) (57 mg, 0.3 mmol) was treated with 3-pyridylisocyanate as in the procedure described in Example 1. The crude product was recrystallised from ethanol/diethyl ether to give the title compound as a white crystalline solid m.p. =218°–220° C.

NMR (D₆ DMSO) δ: 1.00 (3H, t, J=8), 1.66 (2H, q, J=8), 2.70 (2H, t, J=8), 3.27 (2H, t, J=8), 4.26 (2H, t, J=8), 7.25 (1H, s), 7.42 (1H, m), 7.98 (1H, s), 8.08 (1H, d, J=8), 8.32 (1H, d, J=5), 8.83 (1H, m), 8.89 (1H, s).

Example 34

6-Chloro-5-tert-butyl-1-(3-pyridylcarbamoyl) indoline (E34)

6-Chloro-5-tert-butylindoline (D56) (0.21 g, 1.01 mmol) was treated with 3-pyridylisocyanate as in the procedure

Example 35

4-Chloro-5-tert-butyl-1-(3-pyridylcarbamoyl) indoline (E35)

4-Chloro-5-tert-butylindoline (D57) (0.45 g, 3.04 mmol) was treated with 3-pyridylisocyanate as in the procedure described in Example 1. The product was recrystallised from ethanol/diethyl ether to give the title compound (0.46 g, 58%) as a white crystalline solid m.p.=174°–176° C.

NMR ($D_6$ DMSO) δ: 1.42 (9H, s), 3.21 (2H, t, J=8), 4.19 (2H, t, J=8), 7.25 (1H, d, J=7), 7.33 (1H, m), 7.70 (1H, d, J=7), 7.99 (1H, d, J=9), 8.22 (1H, d, 5), 8.77 (2H, m).

Found: C, 65.28; H. 6.07; N, 12.92% $C_{18}H_{20}N_3OCl$ requires: C, 65.55; H, 6.11; N, 12.74%.

Example 36

6-Chloro-5-isopropyl-1-(3-pyridylcarbamoyl) indoline (E36)

6-Chloro-5-isopropylindoline (D58) (0.4 g, 2.05 mmol) was treated with 3-pyridylisocyanate as in the procedure described in Example 1. The product was recrystallised from ethanol/diethyl ether to give the title compound (0.36 g, 57%) as a white crystalline solid m.p.=183°–185° C.

NMR ($D_6$ DMSO) δ: 1.19 (6H, d, J=8), 2.18 (2H, t, J=8), 3.23 (1H, m, J=8), 4.15 (2H, t, J=8), 7.24 (1H, s), 7.33 (1H, m), 7.86 (1H, s), 7.98 (1H, d, J=9), 8.22 (1H, d, J=5), 8.73 (1H, m), 8.78 (1H, s).

Found: C, 64.49; H, 5.78; N, 13.49% $C_{17}H_{18}N_3OCl$ requires: C, 64.66; H, 5.75; N, 13.31%

Example 37

6-Chloro-5-vinyl-1-(3-pyridylcarbamoyl)indoline (E37)

6-Chloro-5-vinylindoline (D62) (0.13 g, crude) was treated with 3-pyridylisocyanate as in the procedure described in Example 1. The crude product was recrystallised from ethanol/diethyl ether to give the title compound (22 mg) as a yellow crystalline solid m.p. 195°–200° C.

NMR ($D_4$ MeOD) δ: 3.20 (2H, t, J=7), 4.18 (2H, t, J=7), 5.25 (1H, d, J=10), 5.68 (1H, d, J=10), 7.00 (1H, m), 7.36 (3H, m), 7.90 (1H, s), 8.00 (2H, m).

Example 38

6-Chloro-5-ethylthio-1-(3-pyridylcarbamoyl) indoline (E38)

6-Chloro-5-ethylthioindoline (D64) (0.18 g, 0.85 mmol) was treated with 3-pyridylisocyanate as in the procedure described in Example 1. The crude product was recrystallised from ethanol/diethyl ether to give the title compound (0.14 g, 48%) as a white crystalline solid m.p.=225°–226° C.

NMR ($D_4$ MeOD) δ: 1.25 (3H, t, J=7), 2.90 (2H, q, J=7), 3.20 (2H, t, J=7), 4.15 (2H, t, J=7), 7.24 (1H, s), 7.37 (1H, m), 7.95 (1H, s), 8.02 (1H, d, J=8), 8.20 (1H, d, J=5), 8.67(1H, s).

Example 39

6-Chloro-5-isopropylthio-1-(3-pyridylcarbamoyl) indoline (E29)

6-Chloro-5-isopropylthioindoline (D66) (0.35 g, 1.52 mmol) was treated with 3-pyridylisocyanate as in the procedure described in Example 1. The crude product was recrystallised from ethanol/diethyl ether to give the title compound (0.33 g, 61%) as a white crystalline solid m.p. 199°–201° C.

NMR (DMSO $D_6$) δ: 1.25 (6H, d, J=7), 3.20 (2H, t, J=8), 3.41 (1H, m, J=7), 4.20 (2H, t, J=8), 7.35 (1H, m), 7.40 (1H, s), 7.96 (1H, s), 8.00 (1H, m), 8.26 (1H, d, J=5), 8.75 (1H, m), 8.86 (1H, s).

Example 40

Methyl-6-chloro-1-(3-pyridylcarbamoyl)-indoline-5-carboxylate (E40)

This was prepared as a white crystalline solid (0.17 g, 57%) from methyl-6-chloroindoline-5-carboxylate using the same method as for Example 2 m.p. >210° C., NMR (DMSO) δ: 3.20 (2H, t, J=8), 3.80 (31, s), 4.25 (2H, t, J=8), 7.35 (1H, m), 7.70 (1H, s), 7.95 (1H, s), 7.80 (1H, m), 8.25 (1H, m), 8.75 (1H, d, J=2), 8.95 (1H, s).

m.e. 331 $C_{16}H_{14}N_3O_3Cl$ requires 331 Found: C, 57.82; H, 4.35; N, 12.63 $C_{16}H_{14}N_3O_3Cl$ requires C, 57.93; H, 4.25; N, 12.67

Example 41

6-Chloro-5-iodo-1-(3-pyridylcarbamoyl)-indoline (E41)

This was prepared from 6-chloro-5-iodoindoline (D10) using the general method as for (Example 2), giving the title compound as a white crystalline solid, m.p. >200° C.

NMR (DMSO) δ: 3.15 (2H, t, J=8), 4.20 (2H, t, J=8), 7.35 (1H, m), 7.75 (1H, s), 7.95 (1H, m), 8.00 (1H, s), 8.25 (1H, m), 8.70 (1H, m), 8.85 (1H, s). m/e 399 $C_{14}H_{11}ClIN_3O$ requires 399

Example 42

6-Chloro-5-methyl-1-(5-bromo-3-pyridylcarbamoyl) -indoline (E42)

The title compound was prepared from 5-bromo-nicotinoyl azide and 6-chloro-5-methyl indoline (D10) using the same procedure as for Example 2, affording the product as a white solid (0.47 g, 85%)

m/e 366 $C_{15}H_{13}BrClN_3O$ requires 366 Found: C, 49.22; H, 3.74; N, 11.45 $C_{15}H_{13}BrClN_3O$ requires C, 49.14; H, 3.57; N, 11.46

Example 43

6-Bromo-5-propylthio-1-(3-pyridylcarbamoyl) indoline (E43)

6-Bromo-5-propylthioindoline (D83) (0.095 g, 0.35 mmol) was treated with 3-pyridylisocyanate as in the procedure described in Example 1. The product was recrystallised from ethanol/diethyl ether to give the title compound (0.089 g, 65%) as a white crystalline solid m.p. 224°–226° C.

NMR ($D_6$ DMSO) δ: 1.00 (3H, t, J=7), 1.59 (2H, sextuplet, J=7), 2.91 (2H, t, J=7), 3.18 (2H, t, J=8), 4.18(2H,

--- described in Example 1. The product was recrystallised from ethanol/diethyl ether to give the title compound (0.12 g, 35%) as a white crystalline solid m.p.=200° C.

NMR ($D_6$ DMSO) δ: 1.40 (9H, s), 3.15 (2H, t, J=8), 4.15 (2H, t, J=8), 7.30 (1H, s), 7.33 (1H, m), 7.85 (1H, s), 7.98 (1H, d, J=9), 8.22 (1H, d, J=5), 8.73 (1H, m), 8.78 (1H, s).

Found: C, 65.13; H, 6.03; N, 13.15% $C_{18}H_{20}N_3OCl$ requires: C, 65.55; H, 6.11; N, 12.74% t, J=8),7.29 (1H, s), 7.34 (1H, dd, J=4, 7),7.98 (1H, d, J=7), 8.10 (1H, s), 8.24 (1H, d, J=4), 8.73 (1H, m), 8.82 (1H, s).

Example 44

6-Bromo-5-ethylthio-1-(3-pyridylcarbamoyl) indoline (E44)

6-Bromo-5-ethylthioindoline (D84) (0.28 g, 1.09 mmol) was treated with 3-pyridylisocyanate as in the procedure described in Example 1. The product was recrystallised from ethanol/diethyl ether to yield the title compound (0.29 g, 70%) as an off-white crystalline solid m.p. 226°–227° C.

NMR ($D_6$ DMSO) δ: 1.24 (3H, t, J=7), 2.95 (2H, q, J=7), 3.19 (2H, t, J=8), 4.18 (2H, t, J=8), 7.29 (1H, s), 7.34 (1H, dd, J=4, 7), 7.98 (1H, d, J=7), 8.11 (1H, s), 8.23 (1H, d, J=4), 8.73 (1H, m), 8.82 (1H, s).

Example 45

6-Bromo-5-methylthio-1-(3-pyridylcarbamoyl) indoline (E45)

6-Bromo-5-methylthioindoline (D85) (0.26 g, 1.06 mmol) was treated with 3-pyridylisocyanate as in the procedure described in Example 1. The product was recrystallised from ethanol to afford the title compound (0.27 g, 71%) as a white crystalline solid m.p. 242°–244° C.

NMR ($D_6$ DMSO) δ: 2.47 (3H, s), 3.19 (2H, t, J=8), 4.18 (2H, t, J=8), 7.19 (1H, s), 7.34 (1H, dd, J=4,7), 7.97 (1H, d, J=7), 8.09 (1H, s), 8.24 (1H, d, J=4), 8.73 (1H, m), 8.81 (1H, s).

Example 46

Pharmaceutical compositions for oral administration may be prepared by combining the following:

1) Solid Dosage Formulation

| | % w/w |
|---|---|
| Compound of formula 1 | 10% |
| Magnesium stearate | 0.5% |
| Starch | 2.0% |
| HPM cellulose | 1.0% |
| Microcrystalline cellulose | 86.5% |

The mixture may be compressed to tablets, or filled into hard gelatin capsules. The tablet may be coated by applying a suspension of film former (e.g. HPM cellulose), pigment (e.g. titanium dioxide) and plasticiser (e.g. diethyl phthalate) and drying the film by evaporation of the solvent. The film coat can comprise 2.0% to 6.0% of the tablet weight, preferably about 3.0%.

2) Capsule

| | % w/w |
|---|---|
| Compound of formula 1 | 20% |
| Polyethylene glycol | 80% |

The medicinal compound is dispersed or dissolved in the liquid carrier, with a thickening agent added, if required. The formulation is then enclosed in a soft gelatin capsule by suitable technology.

Example 44

A pharmaceutical composition for parenteral administration may be prepared by combining the following:

| | Preferred Level |
|---|---|
| Compound of formula 1 | 1.0% |
| Saline | 99.0% |

The solution is sterilised and sealed in sterile containers.

Pharmacological Data

[$^3$H]-mesulergine binding to rat or human 5-HT$_{2C}$ clones expressed in 293 cells in vitro Compounds were tested following the procedure outlined in WO 94/04533. The compounds of examples 1 to 42 have pKi values of 6.1 to 8.7.

Reversal of MCPP-induced Hypolocomotion

Compounds were tested following the procedure outlined in WO 94/04533. The compounds of examples 2, 29, 38 and 40 have ID$_{50's}$ of 0.6 to 15.9 mg/kg p.o.

Geller Seifter Procedure

The compound of example 2 was tested following the procedure outlined in WO 94/04533. The compound showed a significant increase in punished responding in the dose range 0.5–10 mg/kg p.o.

What is claimed is:

1. A compound of formula (I) or a salt thereof:

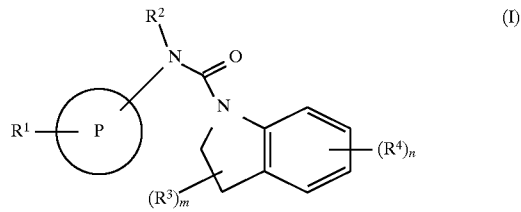

wherein: P represents pyridyl;

R$^1$ is hydrogen, C$_{1-6}$ alkyl, halogen, CF$_3$, NR$^7$R$^8$ or OR$^9$ where R$^7$, R$^8$ and R$^9$ are independently hydrogen, C$_{1-6}$ alkyl or arylC$_{1-6}$alkyl;

R$^2$ is hydrogen or C$_{1-6}$ alkyl;

R$^3$ is C$_{1-6}$ alkyl;

n is 0 to 3;

m is 0 or 1; and

R$^4$ groups are independently C$_{1-6}$ alkyl optionally substituted by one or more halogen atoms, C$_{2-6}$ alkenyl, C$_{2-6}$ alkynyl, C$_{3-6}$ cycloalkyl, C$_{3-6}$ cycloalkyl-C$_{1-6}$ alkyl, C$_{1-6}$ alkylthio, C$_{3-6}$cycloalkylthio, C$_{3-6}$ cycloalkyl-C$_{1-6}$ alkylthio, halogen, nitro, CF$_3$, OCF$_3$, SCF$_3$, SO$_2$CF$_3$, SO$_2$F, formyl, C$_{2-6}$ alkanoyl, NR$^7$R$^8$, CONR$^7$R$^8$, or OR$^9$ where R$^7$, R$^8$ and R$^9$ are as defined for R$^1$, CO$_2$R$^{10}$ where R$^{10}$ is hydrogen or C$_{1-6}$ alkyl or R$^4$ is phenyl or thienyl optionally substituted by C$_{1-6}$ alkyl, halogen, CF$_3$, NR$^7$R$^8$ or OR$^9$.

2. A compound according to claim 1 in which R$^1$ is hydrogen.

3. A compound according to claim 1 in which R$^2$ is hydrogen and m is 0.

4. A compound according to claim 1 in which R$^4$ is C$_{1-6}$alkyl or C$_{1-6}$alkylthio and n is 2.

5. A compound according to claim 1 which is:

5-Ethylthio-1-(3-pyridylcarbamoyl)indoline,

6-Chloro-5-methyl-1-(3-pyridycarbamoyl)indoline,

6-Chloro-5-methyl-1-(3-pyridylcarbamoyl)indoline and 4-chloro-5-methyl-1-(3-pyridylcarbamoyl)indoline,
5-(N,N-Dimethylamino)-1-(3-pyridylcarbamoyl)indoline,
5-Iodo-1-(3-pyridylcarbamoyl)indoline,
5-Nitro-1-(3-pyridylcarbamoyl)indoline,
5-Methylthio-1-(3-pyridylcarbamoyl)indoline,
5-(2-Isoropyl)-1-(3-pyridylcarbamoyl)indoline,
4,6-Dichloro-5-methyl-1-(3-pyridylcarbamoyl)indoline,
6-Fluoro-5-methyl-1-(3-pyridylcarbamoyl)indoline,
6-Iodo-5-methyl-1-(3-pyridylcarbamoyl)indoline,
4-Iodo-5-methyl-1-(3-pyridylcarbamoyl)indoline,
6-Bromo-5-methyl-1-(3-pyridylcarbamoyl)indoline,
4-Bromo-5-methyl-1-(3-pyridylcarbamoyl)indoline,
5-Phenyl-1-(3-pyridylcarbamoyl)indoline,
4,5-Dichloro-1-(3-pyridylcarbamoyl)indoline,
6,7-Dichloro-1-(3-pyridylcarbamoyl)indoline,
5-Chloro-1-(3-pyridylcarbamoyl)indoline,
6-Chloro-1-(3-pyridylcarbamoyl)indoline,
5,6-Dichloro-1-(3-pyridylcarbamoyl)indoline,
5-(3-Thienyl)-1-(3-pyridylcarbamoyl)indoline,
5-Trifluoromethyl-1-(3-pyridylcarbamoyl)indoline,
5-Chloro-6-methyl-1-(3-pyridylcarbamoyl)indoline,
6-Chloro-5-methyl-1-(4-pyridyl-carbamoyl)indoline,
6-Chloro-5-methylthio-1-(3-pyridylcarbamoyl)indoline,
4-Chloro-5-methylthio-1-(3-pyridylcarbamoyl)indoline,
5-Bromo-1-(3-pyridylcarbamoyl)indoline,
6-Chloro-5-ethyl-1-(3-pyridylcarbamoyl)indoline,
6-Chloro-5-propyl-1-(3-pyridylcarbamoyl)indoline,
6-Chloro-5-tert-butyl-1-(3-pyridylcarbamoyl)indoline,
4-Chloro-5-tert-butyl-1-(3-pyridylcarbamoyl)indoline,
6-Chloro-5-isopropyl-1-(3-pyridylcarbamoyl)indoline,
6-Chloro-5-vinyl-1-(3-pyridylcarbamoyl)indoline,
6-Chloro-5-ethylthio-1-(3-pyridylcarbamoyl)indoline,
6-Chloro-5-isopropylthio-1-(3-pyridylcarbamoyl)indoline,
Methyl-6-chloro-1-(3-pyridylcarbamoyl)-indoline-5-carboxylate,
6-Chloro-5-iodo-1-(3-pyridylcarbamoyl)-indoline,
6-Chloro-5-methyl-1-(5-bromo-3-pyridylcarbamoyl)-indoline,
6-Bromo-5-propylthio-1-(3-pyridylcarbamoyl)indoline,
6-Bromo-5-ethylthio-1-(3-pyridylcarbamoyl)indoline,
6-Bromo-5-methylthio-1-(3-pyridylcarbamoyl)indoline,
and pharmaceutically acceptable salts thereof.

6. A pharmaceutical composition which comprises a compound according to claim 1 and a pharmaceutically acceptable carrier or excipient.

* * * * *